(12) United States Patent
Muchhala et al.

(10) Patent No.: US 10,602,940 B1
(45) Date of Patent: Mar. 31, 2020

(54) SYSTEMS, DEVICES, SOFTWARE, AND METHODS FOR DIAGNOSIS OF CARDIAC ISCHEMIA AND CORONARY ARTERY DISEASE

(71) Applicant: Genetesis, Inc., Mason, OH (US)

(72) Inventors: Raj Muchhala, Mason, OH (US); Emmanuel T. Setegn, Mason, OH (US); Benjamin Donaldson Moore, Mason, OH (US); Peeyush Shrivastava, Mason, OH (US)

( * ) Notice: Subject to any disclaimer, the term of this patent is extended or adjusted under 35 U.S.C. 154(b) by 0 days.

(21) Appl. No.: 16/197,264

(22) Filed: Nov. 20, 2018

(51) Int. Cl.
| | |
|---|---|
| A61B 5/00 | (2006.01) |
| A61B 5/04 | (2006.01) |
| A61B 5/0472 | (2006.01) |
| A61B 5/0468 | (2006.01) |
| A61B 5/024 | (2006.01) |
| A61B 5/0265 | (2006.01) |
| A61B 5/02 | (2006.01) |
| A61B 5/046 | (2006.01) |
| G16H 50/20 | (2018.01) |

(52) U.S. Cl.
CPC ........ *A61B 5/04007* (2013.01); *A61B 5/0265* (2013.01); *A61B 5/02405* (2013.01); *A61B 5/0468* (2013.01); *A61B 5/0472* (2013.01); *A61B 5/02007* (2013.01); *A61B 5/046* (2013.01); *G16H 50/20* (2018.01)

(58) Field of Classification Search
CPC ............ A61B 5/04007; A61B 5/02405; A61B 5/0265; A61B 5/02007; A61B 5/046; G16H 50/20
USPC .................................................. 600/300, 516
See application file for complete search history.

(56) References Cited

U.S. PATENT DOCUMENTS

| | | | | |
|---|---|---|---|---|
| 5,697,369 | A * | 12/1997 | Long, Jr. ................. | A61B 5/04 600/407 |
| 5,715,821 | A * | 2/1998 | Faupel ..................... | A61B 5/04 600/302 |
| 6,390,098 | B1 * | 5/2002 | LaFontaine ........ | A61B 18/1492 128/898 |
| 7,270,670 | B1 * | 9/2007 | Yencho ............. | A61B 5/02007 600/207 |
| 7,395,107 | B2 * | 7/2008 | Ishiyama ........... | A61B 5/04007 600/409 |
| 8,315,713 | B2 * | 11/2012 | Burnes ................ | A61N 1/0558 607/116 |
| 8,323,188 | B2 * | 12/2012 | Tran .................... | A61B 5/0022 600/300 |

(Continued)

OTHER PUBLICATIONS

Watanabe, Shigeyuki & Yamada, Satsuki. (Dec. 2008). Magnetocardiography in Early Detection of Electromagnetic Abnormality in Ischemic Heart Disease. Journal of Arrhythmia. 24. 4-17. 10.4020/jhrs.24.4.*

(Continued)

*Primary Examiner* — Carl H Layno
*Assistant Examiner* — Michael J Lau
(74) *Attorney, Agent, or Firm* — Wilson Sonsini Goodrich & Rosati

(57) ABSTRACT

Described herein are methods, software, systems and devices for detecting the presence of an abnormality in an organ, tissue, body, or portion thereof of a subject by analysis of the electromagnetic fields generated by the organ, tissue, body, or portion thereof.

15 Claims, 18 Drawing Sheets
(10 of 18 Drawing Sheet(s) Filed in Color)

(56) References Cited

U.S. PATENT DOCUMENTS

| | | | |
|---|---|---|---|
| 2004/0243022 A1* | 12/2004 | Carney | A61B 5/0086 600/552 |
| 2006/0234304 A1 | 10/2006 | Amann-Zalan et al. | |
| 2007/0276270 A1* | 11/2007 | Tran | A61B 5/0022 600/508 |
| 2009/0177107 A1 | 7/2009 | Guion-Johnson | |
| 2009/0281413 A1* | 11/2009 | Boyden | A61B 5/0059 600/407 |
| 2010/0004708 A1* | 1/2010 | Jahns | A61N 1/056 607/3 |
| 2010/0249620 A1* | 9/2010 | Cho | A61B 5/02007 600/504 |
| 2011/0119212 A1* | 5/2011 | De Bruin | A61B 5/00 706/12 |
| 2012/0289954 A1* | 11/2012 | Lam | A61B 17/3207 606/33 |
| 2013/0317337 A1* | 11/2013 | Wu | A61B 5/04007 600/409 |
| 2013/0324832 A1* | 12/2013 | Wu | A61B 5/04005 600/409 |
| 2014/0107511 A1* | 4/2014 | Banet | G06Q 50/24 600/516 |
| 2014/0308930 A1* | 10/2014 | Tran | H04W 4/18 455/414.1 |
| 2014/0343396 A1 | 11/2014 | Sternickel et al. | |
| 2014/0379269 A1* | 12/2014 | Schmitt | A61B 5/6852 702/19 |
| 2016/0287166 A1* | 10/2016 | Tran | H04B 1/3827 |
| 2017/0135633 A1* | 5/2017 | Connor | A61B 5/4866 |
| 2017/0332918 A1* | 11/2017 | Keane | A61B 5/0422 |
| 2018/0000371 A1 | 1/2018 | Gupta et al. | |
| 2018/0064400 A1 | 3/2018 | Chbat et al. | |
| 2018/0070841 A1* | 3/2018 | Honore | A61B 5/02438 |
| 2018/0078146 A1* | 3/2018 | Shadforth | G16H 30/40 |
| 2018/0235470 A1* | 8/2018 | Johnson | A61B 5/0006 |

OTHER PUBLICATIONS

International Application No. PCT/US2018/062113 International Search Report and Written Opinion dated Jan. 31, 2019.
Amsterdam et al.: Testing of low-risk patients presenting to the emergency department with chest pain; a scientific statement from the American Heart Association. Circulation.; 122(17):1756-76 (2010).
Arbab-Zadeh, Armin: Stress testing and non-invasive coronary angiography in patients with suspected CAD: time for a new paradigm. Heart Int. 2012;7(1):e2.
Heron, Melonie: Leading Causes for 2014. Natl Vital Stat Rep.; 65(5):1-96 (2016).
Moseley et al.: Emergency department observation units and the older patient. Clin Geriatr Med.; 29(1):71-89 (2013).
Reinhardt et al.: Noninvasive Cardiac Testing vs Clinical Evaluation Alone in Acute Chest Pain: A Secondary Analysis of the ROMICAT-II Randomized Clinical Trial. JAMA Intern Med.; 178(2):212-9 (2018).

* cited by examiner

SYSTEMS, DEVICES, SOFTWARE, AND METHODS FOR DIAGNOSIS OF CARDIAC ISCHEMIA AND CORONARY ARTERY DISEASE

BACKGROUND

Human and animal tissue is associated with an electromagnetic field (EMF) due to electrical currents passing through said tissue. Abnormalities in electromagnetic fields can be indicative of serious health conditions.

SUMMARY

Described herein are systems, devices, software, and methods for using an EMF to evaluate an individual. An EMF associated with a heart of an individual may be sensed and analyzed to reveal a status of a heart of the individual. For example, an EMF of an individual may be used to determine whether ischemia is present in a heart of an individual and whether the ischemia is caused by coronary artery disease (CAD). Likewise, if CAD is present, an EMF can be used to determine the severity of the coronary disease that is present.

More specifically, described herein are systems, devices, software, and methods for sensing an EMF and analyzing to make a determination with respect to a heart of an individual. In some embodiments, an EMF that is generated by a heart of an individual is sensed using an EMF sensor and analyzed by a machine learning algorithm which is trained to determine whether ischemia and/or CAD is present in the heart of the individual. In some of these embodiments, the machine learning algorithm is further configured to determine a severity of CAD in the individual.

In some embodiments, a machine learning software module is trained using EMF data and data relating to an individual including their records and data relating to the organs and/or tissue in the body of the individual. Abnormality data includes the presence or absence of an abnormality within an organ, tissue, body, or portion thereof, and said abnormalities are identified along with any known resulting or associated disease, disorder or condition. Data relating to an individual includes demographic data, medical image data, clinical data (e.g. from a health record, including an Electronic Health Record), encoded data, and encoded features, or metrics derived from an electromagnetic field EMF data includes EMF measurements and simulations of EMF measurements. The machine learning software module described herein, in some embodiments, is trained on both EMF data and the corresponding abnormality data (i.e. that corresponds to an EMF data), such that the machine learning software module is able to analyze new EMF data and determine whether an abnormality is present based on training. Furthermore, the machine learning software module may determine a condition associated with the detected abnormality.

Described herein are methods, software, systems and devices for detecting the presence of an abnormality in an organ, tissue, body, or portion thereof of a subject by analysis of the EMFs generated by the organ, tissue, body, or portion thereof. In some embodiments, EMF data is used to generate one or more of a medical image, clinical data, and encoded data. In these embodiments, medical image data, clinical data, encoded data and/or other features or metrics derived from the EMF data are used as inputs to train a machine learning algorithm which is configured to identify a presence of an abnormality in an individual. Said abnormality may be related to an organ from which an EMF is sensed or other organs or systems in an individual. In some embodiments, a machine learning algorithm is configured to determine or predict an abnormality score for an individual.

Described herein is a diagnostic system configured to determine if cardiac ischemia is present in an individual, said diagnostic system comprising: an electromagnetic field sensor configured to sense an electromagnetic field measurement associated with a heart of the individual; a processor operably coupled to the electromagnetic field sensor; and a non-transitory computer-readable storage media encoded with software comprising a trained machine learning software module, wherein said software is executable by the processor and causes the processor to: receive the electromagnetic field measurement from the electromagnetic field sensor; and determine whether ischemia is present in the heart of the individual. In some embodiments, the software is further configured to cause the processor to determine whether the individual has a coronary artery occlusion. In some embodiments, the coronary artery occlusion is determined to be a degree of occlusion of >50%. In some embodiments, the coronary artery occlusion is determined to be a degree of occlusion of >50% and <70%. In some embodiments, the coronary artery occlusion is determined to be a degree of occlusion of >70%. In some embodiments, the coronary artery occlusion is determined to be a degree of occlusion of >70%. In some embodiments, the coronary artery occlusion is determined to be a degree of occlusion of >90%. In some embodiments, the individual has at least one negative troponin value. In some embodiments, the individual has a normal electrocardiogram. In some embodiments, a sensor array and wherein the electromagnetic field sensor is positioned within the array. In some embodiments, the electromagnetic field sensor comprises an optically pumped magnetometer or a superconducting quantum interference device type sensor. In some embodiments, the trained machine learning software module has access to stored data comprising a plurality of electromagnetic field values sensed from a plurality of individuals within a population. In some embodiments, the stored data comprises a plurality of health data values associated with the plurality of individuals. In some embodiments, the trained machine learning software module has access to data used to train the trained machine learning software module. In some embodiments, the data used to train the trained machine learning software module comprises heart related data. In some embodiments, the heart related data comprises an electromagnetic field associated with a heart of the individual. In some embodiments, the processor is further configured to translate the electromagnetic measurement to a waveform. In some embodiments, the software is further configured to cause the processor to determine a therapy or other course of action for treating the individual or for providing clinical decision making support. In some embodiments, the software is further configured to determine a triage pathway for a patient.

Described herein is a diagnostic method comprising: receiving an electromagnetic field measurement associated with the heart of an individual from an electromagnetic field sensor operably coupled to a sensing device comprising a processor and a trained machine learning software module; determining, using the processor, a presence of ischemia in the heart of individual based on the electromagnetic field measurement. In some embodiments, the software is further configured to cause the processor to determine whether the individual has a coronary artery occlusion. In some embodiments, the coronary artery occlusion is determined to be a degree of occlusion of >50%. In some embodiments, the coronary artery occlusion is determined to be a degree of occlusion of >50% and <70%. In some embodiments, the coronary artery occlusion is determined to be a degree of occlusion of >70%. In some embodiments, the coronary artery occlusion is determined to be a degree of occlusion of >70%. In some embodiments, the coronary artery occlusion is determined to be a degree of occlusion of >90%. In some embodiments, the individual has at least one negative troponin value. In some embodiments, the individual has a normal electrocardiogram. In some embodiments, the sensing device comprises a sensor array and wherein the electromagnetic field sensor is positioned within the array. In some embodiments, the electromagnetic field sensor comprises an optically pumped magnetometer or a superconducting quantum interference device type sensor. In some embodiments, the method comprises accessing, by the trained machine learning software module, stored data comprising a plurality of electromagnetic field values sensed from a plurality of individuals within a population. In some embodiments, the stored data comprises a plurality of health data values associated with the plurality of individuals. In some embodiments, the method comprises accessing, by the trained machine learning software module, data used to train the trained machine learning software module. In some embodiments, the data used to train the trained machine learning software module comprises heart related data. In some embodiments, the heart related data comprises an electromagnetic field associated with a heart of the individual. In some embodiments, the processor is further configured to translate the electromagnetic field measurement to a waveform. In some embodiments, the software is further configured to cause the processor to determine a therapy or other course of action for treating the individual or for providing clinical decision making support. In some embodiments, the software is further configured to determine a triage pathway for a patient.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
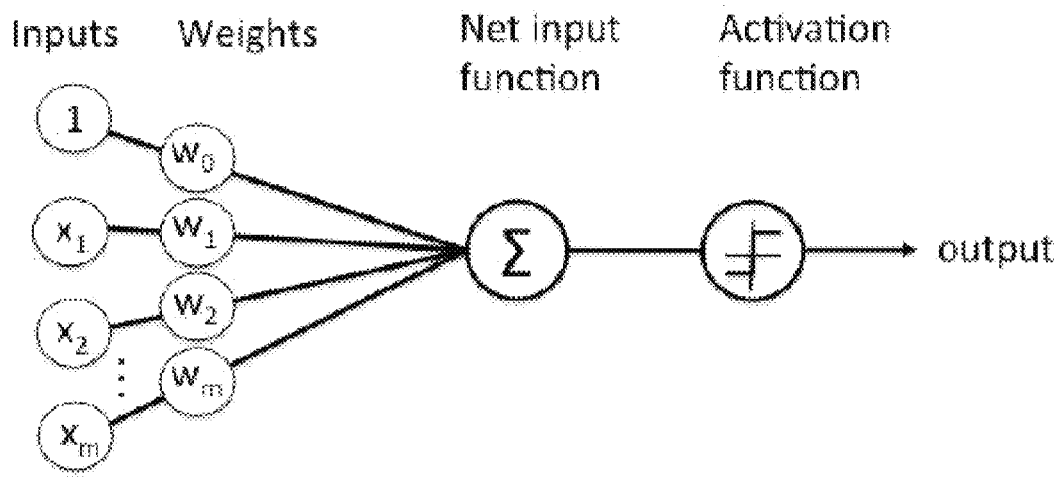
FIGS. 1A and 1B show schematic examples of neural network architecture in terms of flow of data within the neural network.

Described herein are systems, devices, software, and methods for determining an abnormality in an individual by sensing and analyzing EMF data associated with the individual. More specifically, described herein are systems, devices, software, and methods for evaluating a heart of an individual for the presence of an abnormality, disease, or pre-disease state. In some embodiments, an EMF is sensed by an EMF sensor and then the EMF is analyzed by a machine learning algorithm which is configured to determine whether ischemia is present in a tissue of a heart. The machine learning algorithm, in some embodiments, is further configured to determine if a coronary artery obstruction is present indicating CAD. The machine learning algorithm, in some embodiments, is further configured to evaluate a degree of coronary artery occlusion or level of severity of same. In some embodiments, the systems, devices, software, and methods described herein are configured to identify a diagnostic modality that should be used as an additional step in evaluating an individual who is found by the systems, devices, software, and methods to have CAD. In some embodiments, the systems, devices, software, and methods described herein are configured to identify a therapy for an individual.

Software Modules

Sensed EMF data, sensed by one or more EMF sensors, is received and analyzed by a software module comprising a machine learning software algorithm (also referred to herein as a machine learning software module).

In general, a software module as described herein comprises computer readable and executable code. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

In general, a machine learning software module as described herein is configured to receive data, analyze data, and generate an output. Non-limiting examples of an output generated by a machine learning software module include an abnormality, a disease state, an imbalance, a diagnosis, a prognosis, a prediction of a change in health status, a therapy suggestion including preventative therapy.

In some embodiments, a machine learning software module is configured to analyze sensed EMF data and generate a hypothesis function based on said sensed data. A hypothesis function generated by a machine learning software module as described herein, in some embodiments, is configured to determine a presence of an abnormality in an individual based on an EMF sensed from the individual and inputted into the machine learning software module. In some embodiments, a hypothesis function generated by a machine learning software module as described herein is configured to determine a prognosis for an individual based on an EMF sensed from the individual and inputted into the machine learning software module. In some embodiments, a hypothesis function is configured to determine a therapy suggestion for an individual based on an EMF sensed from the individual and inputted into the machine learning software module, wherein said therapy does one or more of treat an existing abnormality and prevent the onset of an abnormality. Analysis of EMF data by a machine learning software module, in some embodiments, comprises identification of an abnormality associated with sensed EMF data. For example, a machine learning algorithm as described herein may receive EMF data sensed from an individual and analyze said data to determine that said individual suffers from congestive heart failure.

Described herein are machine learning software modules configured to analyze EMF data using machine learning algorithms such as, for example, machine learning algorithms that utilize one or more neural networks. A neural network is a type of computational system that can learn the relationships between an input data set and a target data set. A neural network is a software representation of a human neural system (e.g. cognitive system), intended to capture "learning" and "generalization" abilities as used by a human. In some embodiments of the software module, the software module comprises a neural network comprising a convolutional neural network. Non limiting examples of structural components of embodiments of the machine learning software described herein include: (deep) convolutional neural networks, (deep) recurrent neural networks, (deep) dilated convolutional neural networks, (deep) fully connected neural networks, deep generative models, and (deep) (restricted) Boltzmann machines.

In some embodiments of the software applications and systems described herein, a machine learning software module comprises a recurrent neural network software module. A recurrent neural network software module is configured to receive sequential data as an input, such as consecutive EMF measurements, and the recurrent neural network software module updates an internal state at every time step.

In some embodiments, a machine learning software module comprises a supervised or unsupervised learning method such as, for example, SVM, random forests, clustering algorithms, gradient boosting, logistic regression, or decision trees.

In some embodiments, a machine learning software module comprises a neural network comprising a Convolutional Neural Network (CNN), Recurrent Neural Network (RNN), dilated CNN, fully connected neural networks, deep generative models and deep restricted Boltzmann machines.

Figure 1B:
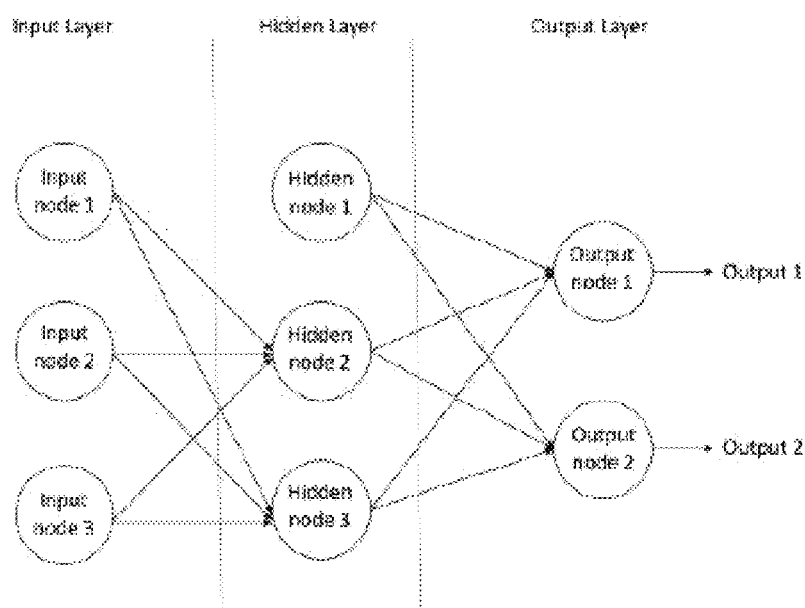

In some embodiments, a neural network is comprised of a series of layers termed "neurons." A typical neuron in a neural network is shown in FIG. 1A. As illustrated in FIG. 1B, in embodiments of neural networks, there is an input layer, to which data is presented; one or more internal, or "hidden," layers; and an output layer. A neuron may be connected to neurons in other layers via connections that have weights, which are parameters that control the strength of the connection. The number of neurons in each layer may be related to the complexity of the problem to be solved. The minimum number of neurons required in a layer may be determined by the problem complexity, and the maximum number may be limited by the ability of the neural network to generalize. The input neurons may receive data from data being presented and transmit that data to the first hidden layer through connections' weights, which are modified during training. The first hidden layer may process the data and transmit its result to the next layer through a second set of weighted connections. Each subsequent layer may "pool" the results from the previous layers into more complex relationships. In addition, whereas conventional software programs require writing specific instructions to perform a function, neural networks are programmed by training them with a known sample set and allowing them to modify themselves during (and after) training so as to provide a desired output such as an output value. After training, when a neural network is presented with new input data, it is configured to generalize what was "learned" during training and apply what was learned from training to the new previously unseen input data in order to generate an output associated with that input.

In some embodiments of a machine learning software module as described herein, a machine learning software module comprises a neural network such as a deep convolutional neural network. In some embodiments in which a convolutional neural network is used, the network is constructed with any number of convolutional layers, dilated layers or fully connected layers. In some embodiments, the number of convolutional layers is between 1-10 and the dilated layers between 0-10. In some embodiments, the number of convolutional layers is between 1-10 and the fully connected layers between 0-10.

Figure 2:
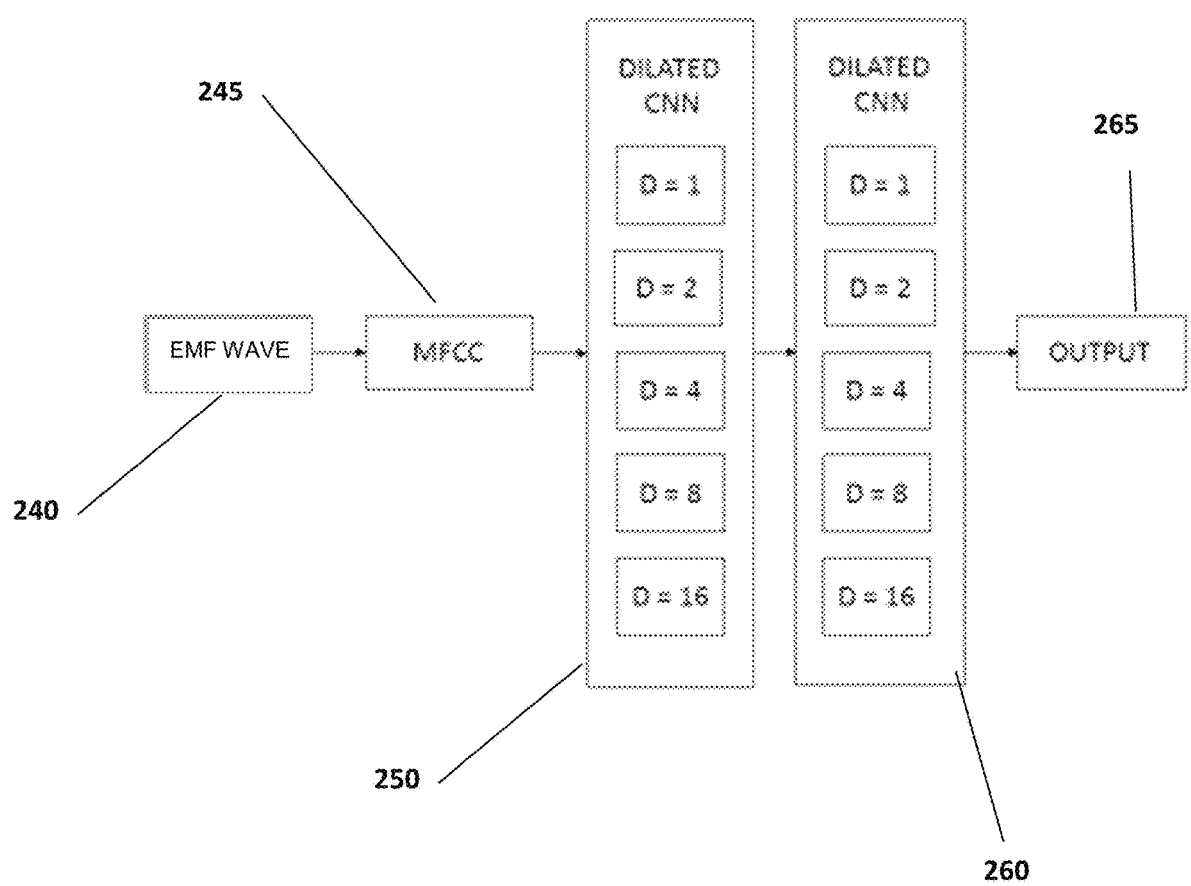
FIG. 2 shows a schematic representing an exemplary machine learning software module.

FIG. 2 shows a flow chart representing the architecture of an exemplary embodiment of a machine learning software module. In this exemplary embodiment, raw EMF 240 of the individual is used to extract the MFCC features 245 which are fed into the deep learning module. The machine learning software module comprises two blocks of Dilated Convolutional neural networks 250, 260 which produce an output 265. Each block has 5 dilated convolution layers with dilation rates D=1, 2, 4, 8, 16. The number of blocks, and the number of layers in each block can increase or decrease, so it is not limited to the configuration portrayed in FIG. 2.

Training Phase

A machine learning software module as described herein is configured to undergo at least one training phase wherein the machine learning software module is trained to carry out one or more tasks including data extraction, data analysis, and output generation.

In some embodiments of the software application described herein, the software application comprises a training module that trains the machine learning software module. The training module is configured to provide training data to the machine learning software module, said training data comprising, for example, EMF measurements and the corresponding abnormality data. In additional embodiments, said training data is comprised of simulated EMF data with corresponding simulated abnormality data. In some embodiments of a machine learning software module described herein, a machine learning software module utilizes automatic statistical analysis of data in order to determine which features to extract and/or analyze from an EMF measurement. In some of these embodiments, the machine learning software module determines which features to extract and/or analyze from an EMF based on the training that the machine learning software module receives.

In some embodiments, a machine learning software module is trained using a data set and a target in a manner that might be described as supervised learning. In these embodiments, the data set is conventionally divided into a training set, a test set, and, in some cases, a validation set. A target is specified that contains the correct classification of each input value in the data set. For example, a set of EMF data from one or more individuals is repeatedly presented to the machine learning software module, and for each sample presented during training, the output generated by the machine learning software module is compared with the desired target. The difference between the target and the set of input samples is calculated, and the machine learning software module is modified to cause the output to more closely approximate the desired target value. In some embodiments, a back-propagation algorithm is utilized to cause the output to more closely approximate the desired target value. After a large number of training iterations, the machine learning software module output will closely match the desired target for each sample in the input training set. Subsequently, when new input data, not used during training, is presented to the machine learning software module, it may generate an output classification value indicating which of the categories the new sample is most likely to fall into. The machine learning software module is said to be able to "generalize" from its training to new, previously unseen input samples. This feature of a machine learning software module allows it to be used to classify almost any input data which has a mathematically formulatable relationship to the category to which it should be assigned.

In some embodiments of the machine learning software module described herein, the machine learning software module utilizes an individual learning model. An individual learning model is based on the machine learning software module having trained on data from a single individual and thus, a machine learning software module that utilizes an individual learning model is configured to be used on a single individual on whose data it trained.

In some embodiments of the machine training software module described herein, the machine training software module utilizes a global training model. A global training model is based on the machine training software module having trained on data from multiple individuals and thus, a machine training software module that utilizes a global training model is configured to be used on multiple patients/individuals.

In some embodiments of the machine training software module described herein, the machine training software module utilizes a simulated training model. A simulated training model is based on the machine training software module having trained on data from simulated EMF measurements. A machine training software module that utilizes a simulated training model is configured to be used on multiple patients/individuals.

In some embodiments, the use of training models changes as the availability of EMF data changes. For instance, a simulated training model may be used if there are insufficient quantities of appropriate patient data available for training the machine training software module to a desired accuracy. This may be particularly true in the early days of implementation, as few appropriate EMF measurements with associated abnormalities may be available initially. As additional data becomes available, the training model can change to a global or individual model. In some embodiments, a mixture of training models may be used to train the machine training software module. For example, a simulated and global training model may be used, utilizing a mixture of multiple patients' data and simulated data to meet training data requirements.

Unsupervised learning is used, in some embodiments, to train a machine training software module to use input data such as, for example, EMF data and output, for example, a diagnosis or abnormality. Unsupervised learning, in some embodiments, includes feature extraction which is performed by the machine learning software module on the input data. Extracted features may be used for visualization, for classification, for subsequent supervised training, and more generally for representing the input for subsequent storage or analysis. In some cases, each training case may consist of a plurality of EMF data.

Machine learning software modules that are commonly used for unsupervised training include k-means clustering, mixtures of multinomial distributions, affinity propagation, discrete factor analysis, hidden Markov models, Boltzmann machines, restricted Boltzmann machines, autoencoders, convolutional autoencoders, recurrent neural network autoencoders, and long short-term memory autoencoders. While there are many unsupervised learning models, they all have in common that, for training, they require a training set consisting of biological sequences, without associated labels.

A machine learning software module may include a training phase and a prediction phase. The training phase is typically provided with data in order to train the machine learning algorithm. Non-limiting examples of types of data inputted into a machine learning software module for the purposes of training include medical image data, clinical data (e.g. from a health record), encoded data, encoded features, or metrics derived from an electromagnetic field. Data that is inputted into the machine learning software module is used, in some embodiments, to construct a hypothesis function to determine the presence of an abnormality. In some embodiments, a machine learning software module is configured to determine if the outcome of the hypothesis function was achieved and based on that analysis make a determination with respect to the data upon which the hypothesis function was constructed. That is, the outcome tends to either reinforce the hypothesis function with respect to the data upon which the hypothesis functions was constructed or contradict the hypothesis function with respect to the data upon which the hypothesis function was constructed. In these embodiments, depending on how close the outcome tends to be to an outcome determined by the hypothesis function, the machine learning algorithm will either adopts, adjusts, or abandon the hypothesis function with respect to the data upon which the hypothesis function was constructed. As such, the machine learning algorithm described herein dynamically learns through the training phase what characteristics of an input (e.g. data) is most predictive in determining whether the features of a patient EMF display any abnormality.

For example, a machine learning software module is provided with data on which to train so that it, for example, is able to determine the most salient features of a received EMF data to operate on. The machine learning software modules described herein train as to how to analyze the EMF data, rather than analyzing the EMF data using pre-defined instructions. As such, the machine learning software modules described herein dynamically learn through training what characteristics of an input signal are most predictive in determining whether the features of an EMF display any abnormality.

In some embodiments, the machine learning software module is trained by repeatedly presenting the machine learning software module with EMF data along with, for example, abnormality data. The term "abnormality data" is meant to comprise data concerning the existence or non-existence of an abnormality in an organ, tissue, body, or portion thereof. Any disease, disorder or condition associated with the abnormality is included in the abnormality data if available. For example, information concerning a subject displaying symptoms of hypertension, ischemia or shortness of breath is included as abnormality data. Information concerning a subject's lack of any irregular health condition is also included as abnormality data. In the case where EMF data is generated by computer simulation, the abnormality data may be used as additional data being used to simulate the organ, tissue, body, or portion thereof. In some embodiments, more than one abnormality is included in the abnormality data. In additional embodiments, more than one condition, disease or disorder is included in the abnormality data.

In some embodiments, training begins when the machine learning software module is given EMF data and asked to determine the presence of an abnormality. The predicted abnormality is then compared to the true abnormality data that corresponds to the EMF data. An optimization technique such as gradient descent and backpropagation is used to update the weights in each layer of the machine learning software module so as to produce closer agreement between the abnormality probability predicted by the machine learning software module, and the presence of the abnormality. This process is repeated with new EMF data and abnormality data until the accuracy of the network has reached the desired level. In some embodiments the abnormality data additionally comprises the type and location of the abnormality. For example, the abnormality data may indicate that an abnormality is present, and that said abnormality is an ischemia of the left ventricle of the heart. In this case, training begins when the machine learning software module is given the corresponding EMF data and asked to determine the type and location of the abnormality. An optimization technique is used to update the weights in each layer of the machine learning software module so as to produce closer agreement between the abnormality data predicted by the machine learning software module, and the true abnormality data. This process is repeated with new EMF data and abnormality data until the accuracy of the network has reached the desired level. In some embodiments, the abnormality data additionally comprises a known resulting or related disease, disorder or condition associated with an identified abnormality. For example, the abnormality data may indicate that the subject possesses an atrial flutter and arterial coronary disease. In cases such as this, training begins when the machine learning software module is given the corresponding EMF data and asked to determine the presence of a condition, disorder or disease. The output data is then compared to the true abnormality data that corresponds to the EMF data. An optimization technique is used to update the weights in each layer of the machine learning software module so as to produce closer agreement between the abnormality probability predicted by the machine learning software module, and the actual abnormality. This process is repeated with new EMF data and abnormality data until the accuracy of the network has reached the desired level. Following training with the appropriate abnormality data given above, the machine learning module is able to analyze an EMF measurement and determine the presence of an abnormality, the type and location of said abnormality and the conditions associated with such.

In some embodiments of the machine learning software modules described herein, the machine learning software module receives EMF data and directly determines the abnormality probability of the subject, wherein the abnormality probability comprises the probability that the EMF measurement is associated with the abnormality of the subject.

In some embodiments, the machine learning software module is trained on a single continuous EMF measurement with corresponding abnormality data over a period of time. This can greatly increase the amount of training data available to train a machine learning software module. For example, in a EMF recording consisting of N continuous 10-second segments with accompanying abnormality data, one can generate at least N*N pairs of such segments to train on.

In some embodiments, an individual's abnormality data is inputted by the individual of the system. In some embodiments, an individual's abnormality data is inputted by an entity other than the individual. In some embodiments, the entity can be a healthcare provider, healthcare professional, family member or acquaintance. In additional embodiments, the entity can be the instantly described system, device or an additional system that analyzes EMF measurements and provides data pertaining to physiological abnormalities.

In some embodiments, a strategy for the collection of training data is provided to ensure that the EMF measurements represent a wide range of conditions so as to provide a broad training data set for the machine learning software module. For example, a prescribed number of measurements during a set period of time may be required as a section of a training data set. Additionally these measurements can be prescribed as having a set amount of time between measurements. In some embodiments, EMF measurements taken with variations in a subject's physical state may be included in the training data set. Examples of physical states include accelerated heart rate and enhanced brain signaling. Additional examples include the analysis of a subjects EMF data under the influence of medication or during the course of medical treatment.

In some embodiments, training data may be generated by extracting random overlapping segments of EMF measurements performed by the subject. In some embodiments, training examples can be provided by measurement recordings, models or algorithms that are independent of the subject. Any mixture or ratio of subject and non-subject training measurements can be used to train the system. For example, a network may be trained using 5 EMF segments extracted from a subject's measurements, and 15,000 EMF segments taken from another subject's recordings. Training data can be acquired using two different methods. The first method is to directly measure the EMF measurements over a subject's chest. The second method involves creating an accurate electro-anatomical model of the heart. This electro-anatomical model can be used to generate EMF measurements of both healthy and diseased subjects. The measurements are acquired by applying the Biot-Savart Law. This calculates the magnetic field vector at a given point in space, caused by a specific movement of current. After the EMF measurements have been acquired or calculated, they are fed into the network with a classification label, describing both the presence and location of diseased tissue.

In general, a machine learning algorithm is trained using a large patient database of medical image and/or clinical data and/or encoded data from one or more EMF measurements and/or any features or metrics computed from the above said data with the corresponding ground-truth values. The training phase constructs a transformation function for predicting probability of an abnormality in an unknown patient's organ, tissue, body, or portion thereof by using the medical image and/or clinical data and/or encoded data from the one or more EMF measurements and/or any features or metrics computed from the above said data of the unknown patient. The machine learning algorithm dynamically learns through training what characteristics of an input signal are most predictive in determining whether the features of a patient EMF data display any abnormality. A prediction phase uses the constructed and optimized transformation function from the training phase to predict the probability of an abnormality in an unknown patient's organ, tissue, body, or portion thereof by using the medical image and/or clinical data and/or encoded data from the one or more EMF measurements and/or any features or metrics computed from the above said data of the unknown patient.

Prediction Phase

Following training, the machine learning algorithm is used to determine, for example, the presence or absence of an abnormality on which the system was trained using the prediction phase. With appropriate training data, the system can identify the location and type of an abnormality, and present conditions associated with such abnormality. For example, an EMF measurement is taken of a subject's brain and appropriate data derived from the EMF measurement is submitted for analysis to a system using the described trained machine learning algorithm. In these embodiments, a machine learning software algorithm detects an abnormality associated with epilepsy. In some embodiments, the machine learning algorithm further localizes an anatomical region associated with an abnormality such as, for example, localizing an area of the brain of an individual associated with epilepsy in the individual based on an EMF measurement of individual.

An additional example, a subject is known to possess arterial ischemia and has EMF measurements recorded before and after treatment with a medication. The medical image and/or clinical data and/or encoded data from the EMF measurements and/or features and/or metrics derived from the said data are submitted for analysis to a system using the described trained machine learning algorithm in order to determine the effectiveness of the medication on abnormal blood flow using the prediction phase.

The prediction phase uses the constructed and optimized hypothesis function from the training phase to predict the probability of an abnormality in an unknown patient's organ, tissue, body, or portion thereof by using the medical image and/or clinical data and/or encoded data from the EMF measurements and/or any features or metrics computed from the above said data of the unknown individual.

In some embodiments, in the prediction phase, the machine learning software module can be used to analyze data derived from its EMF measurement independent of any system or device described herein. In these instances, the new data recording may provide a longer signal window that required for determining the presence of a subject's abnormality. In some embodiments, the longer signal can be cut to an appropriate size, for example 10 seconds and then can be used in the prediction phase to predict the probability of an abnormality of the new patient data.

In some embodiments, a probability threshold can be used in conjunction with a final probability to determine whether or not a given recording matches the trained abnormality. In some embodiments, the probability threshold is used to tune the sensitivity of the trained network. For example, the probability threshold can be 1%, 2%, 5%, 10%, 15%, 20%, 25%, 30%, 35%, 40%, 45%, 50%, 55%, 60%, 65%, 70%, 75%, 80%, 85%, 90%, 95%, 98% or 99%. In some embodiments, the probability threshold is adjusted if the accuracy, sensitivity or specificity falls below a predefined adjustment threshold. In some embodiments, the adjustment threshold is used to determine the parameters of the training period. For example, if the accuracy of the probability threshold falls below the adjustment threshold, the system can extend the training period and/or require additional measurements and/or abnormality data. In some embodiments, additional measurements and/or abnormality data can be included into the training data. In some embodiments, additional measurements and/or abnormality data can be used to refine the training data set.

Input Data

As described herein, a machine learning software module is typically provided with data (input) in order to train the machine learning software module as to how to analyze an EMF to determine, for example, the presence of an abnormality. Input data is also used by a machine learning software module to generate an output.

An input to a machine learning algorithm as described herein, in some embodiments, is data transmitted to the machine learning algorithm by a device or a system which includes an EMF sensor. In some embodiments of the devices, systems, software, and methods described herein, data that is received by a machine learning algorithm software module from an electromagnetic sensor as an input may comprise EMF data expressed in a standard unit of measurement such as, for example, Tesla.

In some embodiments, sensed EMF data comprises an overall or total EMF generated by a body of an individual based on numerous different currents generated by the body of the individual. That is, in some embodiments, one or more EMF sensors sense an EMF that comprises an EMF associated with entire individual and is not specific to a single organ, tissue, body, or portion thereof. Likewise, in some embodiments, an EMF that is sensed from an individual that is associated with a portion of the individual but not specific to a single organ, tissue, body, or portion thereof.

In some embodiments, sensed EMF data comprises an EMF that is in proximity to an individual or a portion of the body of the individual and comprises an EMF associated with a single organ, organ system, or tissue. For example, in some embodiments, one or more EMF sensors are positioned in proximity to a chest of an individual and sense an EMF associated with a heart of the individual. For example, in some embodiments, one or more EMF sensors are positioned in proximity to a head of an individual and sense an EMF associated with a brain of the individual. For example, in some embodiments, one or more EMF sensors are positioned in proximity to a chest of an individual and sense an EMF associated with a cardio-pulmonary system (i.e. the heart and lungs).

In some embodiments, a machine learning software module is configured to receive an encoded length of EMF data as an input and to determine the window length of the input data. For example, an input to a machine learning software module in some embodiments described herein is 100 seconds of encoded EMF data, and the machine learning software module selects a 10 second segment within the 100 second data sample for examination. In some embodiments, the input is segmented into multiple inputs, any number of which is analyzed independently. Any number of these analyses may be used to determine the final output.

In some embodiments, a device, system, or method as described herein is configured to sense and/or receive data comprising data associated with an individual. Data is sensed, in some embodiments, by an electromagnetic field sensor that is a component of a device, system, or method described herein. Data is received, in some embodiments, by transmission of data to a software algorithm as described herein by a source other than an EMF that is a component of a device, system, or method that also includes the software algorithm. That is, data, in some embodiments, is received from a source remote from the device, system, or method that includes the software algorithm. In some embodiments, data that is received comprises stored data. In some embodiments, data that is received comprises data that is generated by a software module. In general, sensed and/or received data comprises an input to a machine learning algorithm as described herein. An input is used to train a machine learning algorithm and/or is used by the machine learning algorithm to carry out an analysis or prediction.

Data as described herein comprises EMF data as well as other information associated with an individual. Non-limiting examples of data used as an input for a machine learning algorithm as described herein includes a medical record (e.g. an electronic health record), a diagnosis, a lab value, a vital sign, a prognosis, an electrocardiogram, a radiology image (including ultrasound, CT scan, Mill, and X-ray), an electroencephalogram, and a pathology report. In some embodiments, two or more different types of data are combined and/or correlated by the software algorithms described herein.

EMF data, in some embodiments, is used to generate other types of data that are used by the software algorithms described herein. For example, EMF data, in some embodiments, is used to generate medical image data which, in some embodiments, is achieved using Magnetic Field Maps (MFM). In some embodiments, EMF data is used to generate medical image data using PseudoCurrent Density (PCD) maps. In some embodiments, EMF data is used to generate medical data using Spatio-Temporal Activation Graphs (STAG).

EMF data, in some embodiments, is used to generate clinical data such as MCG, MEG and MGG measurements.

In some embodiments, input to a software algorithm as described herein comprises EMF data which is encoded into some other form of data and the features or metrics computed from the encoded data such as, for example, MFCC.

In some embodiments, input to a software algorithm as described herein is generated by a computer. For example, in some embodiments, an input to a software algorithm as described herein comprises data generated by computer simulation. In some embodiments, a computer simulation generates an image or other representation of an organ or other tissue (including skin, bone, and blood). In some embodiments, a computer simulation generates an image or representation of a flow of a fluid such as, for example, blood, lymph, or bile. In some embodiments, a computer simulation generates an image or representation of a flow of an electric current. Non-limiting examples of additional inputs generated by a computer simulation include a medical record (e.g. an electronic health record), a diagnosis, a lab value, a vital sign, a prognosis, an electrocardiogram, a radiology image (including ultrasound, CT scan, Mill, and X-ray), an electroencephalogram, and a pathology report.

Data Filtering

In some embodiments of the devices, systems, software, and methods described herein, data that is received by a machine learning algorithm software module from an electromagnetic sensor as an input may comprise EMF data that has been filtered and or modified. In some embodiments, filtering comprises a removal of noise or artifact from a sensed electromagnetic field data. Artifact or noise may comprise, for example, ambient electromagnetic signals that are sensed together with electromagnetic data sensed from an individual.

In some embodiments of the devices, systems, software, and methods described herein, sensed EMF data is filtered prior to and/or after transmission of said data to a processor. Filtering of sensed EMF data may, for example, comprise the removal of ambient signal noise from a sensed EMF data. Signal noise may, for example, comprises ambient EMF data generated by, for example, electronic devices, the earth's magnetosphere, electrical grids, or other individuals (i.e. not individuals whose EMF data is being targeted).

In some embodiments, sensed EMF data is converted to another form of data or signal which then undergoes a signal filtering process. In some embodiments, a device or system includes a processor including software that is configured to convert sensed EMF data to another form of data or signal. The process of converting sensed EMF data to another form of data or signal typically comprises an encoding process, wherein a first form of data is converted into a second form of data or signal.

In some embodiments, sensed EMF data is encoded into an audio signal which undergoes a filtering process. In some embodiments, sensed EMF data is encoded into an audio signal or alternatively, a signal having the morphology of an audio signal.

In some embodiments, sensed EMF data is encoded into an audio signal which is further processed into a Mel-Frequency Cepstrum from which one or more Mel-Frequency Cepstrum Coefficients ("MFCC") are derived. Mel-Frequency Cepstrum ("MFC") represents a short term power spectrum of a sound. It is based on a linear cosine transform of a log power spectrum on a nonlinear mel scale of frequency. Mel-frequency cepstral coefficients ("MFCCs") collectively make up an MFC. These are derived from a type of cepstral representation of the audio. In MFC, frequency bands are equally spaced on the mel-scale as compared to the linearly-spaced frequency bands used in the normal cepstrum. This equally spaced frequency bands allows for better representation of audio.

In some embodiments, a sensed EMF signal is filtered by converting the sensed EMF data into an audio signal or a signal having the morphology of an audio signal wave, and then generating MFCCs.

MFCCs help in identifying the components of the audio signal that are able to differentiate between important content and background noise.

In general, steps for filtering an audio signal derived from sensed EMF data comprise: In a first step, the audio signal is framed into short frames. In a second step, the periodogram estimate of the power spectrum for each frame is calculated. In a third step, a mel filterbank is applied to the power spectrum and sum the energy in each filter. In a fourth step, the logarithm of all the filterbank energies is determined and the DCT of the log filterbank energies is calculated. In a fifth step, only the first 20 DCT coefficients are kept, and the rest are discarded.

Once filtered, the filtered data is transmitted to a machine learning algorithm for analysis. The algorithm described herein is capable of classifying and characterizing the physiological health of human body tissues. The algorithm is designed to analyze input data and determine the presence and location of diseased tissue in the organ(s) recorded by aforementioned sensors.

Devices and Systems

In some embodiments EMF data is sensed using a device or system. In some embodiments, a device or system comprises one or more EMF sensors. In some of these embodiments, the device or system is configured to include a machine learning software module as described herein. In some of these embodiments, the device or system is configured to transmit a sensed EMF to a machine learning software module not included as part of the device or system. EMF data that is sensed using an electromagnetic sensor comprises electromagnetic data associated with a passage of a current through a cell, tissue, and/or organ of an individual, such as, for example, the heart of the individual. Generally, described herein are devices and systems that comprise digital processing devices.

In some embodiments of devices and systems described herein, a device and/or a system comprises a digital processing device configured to run a software application as described herein. In further embodiments, a digital processing device includes one or more hardware central processing units (CPUs) or general purpose graphics processing units (GPGPUs) that carry out the device's functions. In still further embodiments, the digital processing device further comprises an operating system configured to perform executable instructions. In some embodiments, the digital processing device is optionally connected to a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, handheld computers, and tablet computers.

In some embodiments, the digital processing device includes an operating system configured to perform executable instructions. The operating system is, for example, software, including programs and data, which manages the device's hardware and provides services for execution of applications. Non-limiting examples of suitable operating systems include FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing.

In some embodiments, a digital processing device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes, optical disk drives, and cloud computing based storage. In further embodiments, the storage and/or memory device is a combination of devices such as those disclosed herein.

In some embodiments, the digital processing device includes a display to send visual information to a subject. In some embodiments, the digital processing device includes an input device to receive information from a subject. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In still further embodiments, the input device is a combination of devices such as those disclosed herein.

Figure 3:
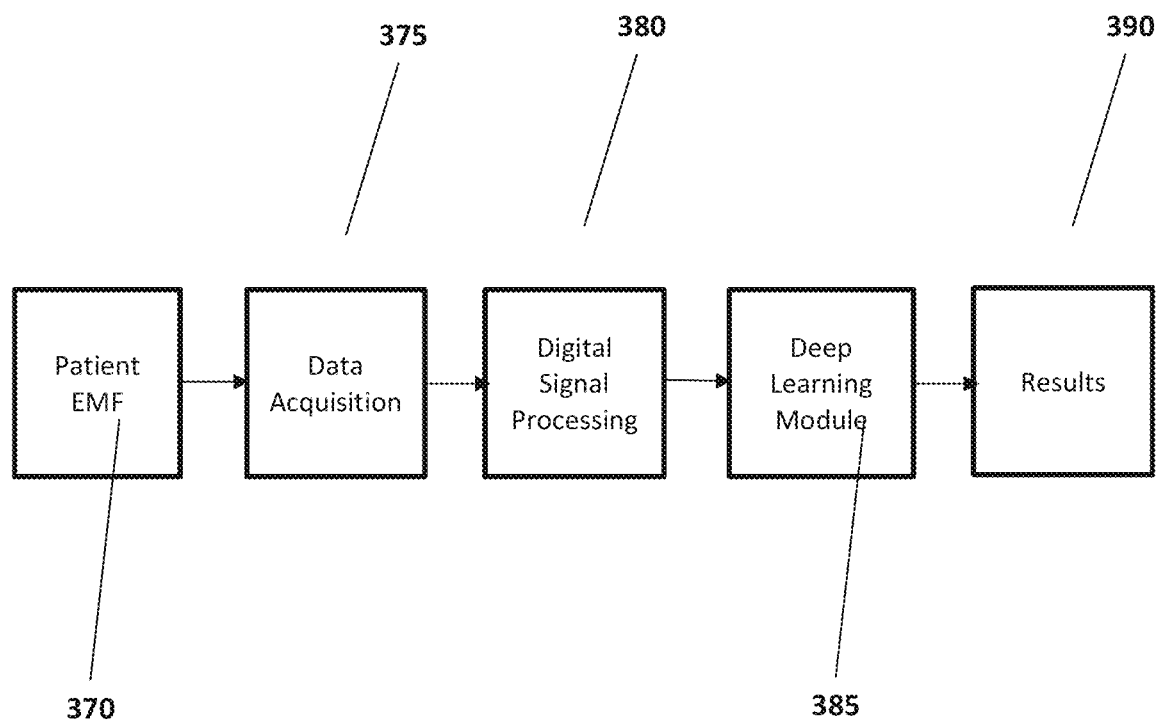
FIG. 3 shows a schematic representation of an exemplary device for sensing an analyzing an EMF.

FIG. 3 shows a schematic representation of an exemplary device for sensing an analyzing an EMF. The patient's organ emits an EMF 370 which is then acquired from the EMF sensing device 375. The data is then processed, filtered and analyzed by a Digital Signal Processing module 380 thereby removing noise if any and extracting important information from the data. The processed data is then fed into the deep learning module 385 consisting of dilated convolutional neural networks. The deep learning module detects ischemia and localizes to a particular region in an organ which comprises a result 390.

In various embodiments, the platforms, systems, media, and methods described herein include a cloud computing environment. In some embodiments, a cloud computing environment comprises a plurality of computing processors.

Figure 4:
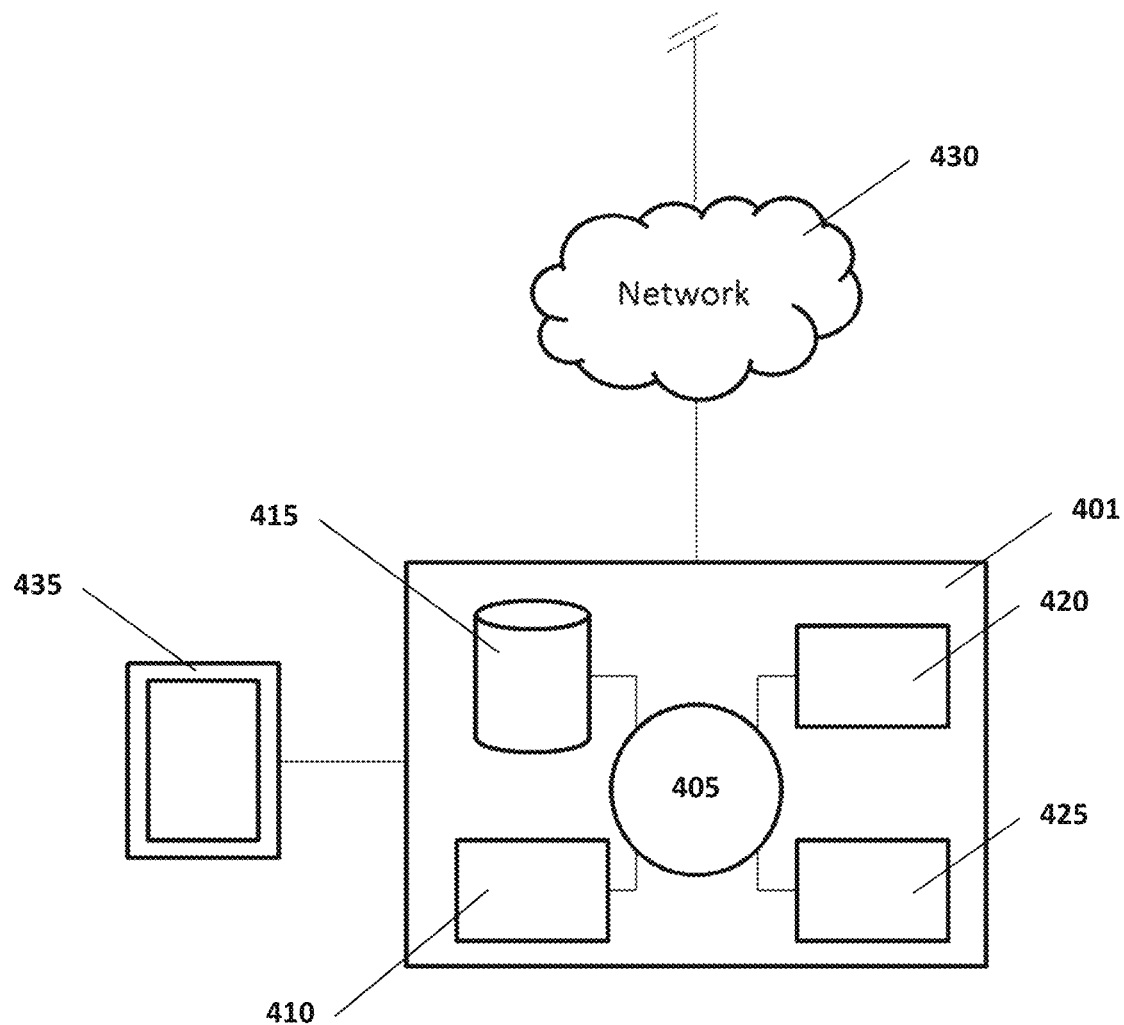
FIG. 4 shows a schematic of an exemplary embodiment of a system comprising a digital processing device.

FIG. 4 shows an exemplary embodiment of a system as described herein comprising a digital processing device 401. The digital processing device 401 includes a software application configured to perform data analysis such as analyzing an electromagnetic field to determine a condition of a subject. The device 401 is configured to run the software application that comprises a machine learning software module including training of the machine learning software module as described herein. In this embodiment, the digital processing device 401 includes a central processing unit (CPU, also "processor" and "computer processor" herein) 405, which can be a single core or multi-core processor, or a plurality of processors for parallel processing. The digital processing device 401 also includes either memory or a memory location 410 (e.g., random-access memory, read-only memory, flash memory), electronic storage unit 415 (e.g., hard disk), communication interface 420 (e.g., network adapter) for communicating with one or more other systems, and peripheral devices 425, such as cache. The memory 410, storage unit 415, interface 420 and peripheral devices 425 are configured to communicate with the CPU 405 through a communication bus (solid lines), such as a motherboard. The digital processing device 401 is, in some embodiments, operatively coupled to a computer network ("network") 430 with the aid of the communication interface 420. The network 430, in some embodiments, comprises the Internet. The network 430 in some embodiments is a telecommunication and/or data network.

The CPU 405 is configured to execute machine-readable instructions embodied in a software application or module. The instructions may be stored in a memory location, such as the memory 410.

The storage unit 415 in some embodiments is configured to store files, such as subject data, e.g., subject preferences, subject programs, and subject EMF data.

Methods as described herein can be implemented by way of machine (e.g., computer processor) executable code stored on an electronic storage location of the digital processing device 401, such as, for example, on the memory 410 or electronic storage unit 415. The machine executable or machine readable code can be provided in the form of a software application or software module. During use, the code can be executed by the processor 405. In some cases, the code can be retrieved from the storage unit 415 and stored on the memory 410 for ready access by the processor 405. In some situations, the electronic storage unit 415 can be precluded, and machine-executable instructions are stored on memory 410.

A remote device 435 is configured to communicate with the digital processing device 401, and may comprises any mobile computing device, non-limiting examples of which include a tablet computer, laptop computer, smartphone, or smartwatch. In some embodiments, a remote device 435 may comprises an integrated sensor or alternatively be coupled to a sensor that is configured to sense EMF data.

In some embodiments of the devices, systems, software, and methods described herein, sensed EMF data is transmitted directly from an electromagnetic sensor to a processor on a computing device that is encoded with a machine learning algorithm configured to analyze the received EMF data.

Described herein are software modules for sensing, analyzing, and optionally filtering data. Software comprising one or more software modules as described herein may, for example, be a component of a device or system that includes one or more sensors comprising an EMF sensor. This sensor records the magnetic fields that are naturally emitted by certain organs during physiological activity. Such organs may include the brain, heart or liver. In some embodiments, this sensor may take the form of a magnetometer, fluxgate, or a superconducting quantum interference device (SQUID) fitted to perform biomagnetic measurements on an organ of interest. More specifically, any sensor or plurality of sensors that is capable of sensing an electromagnetic field is suitable for use with the devices, systems, software, and methods described herein.

In some embodiments of the devices and systems described herein, a device comprises a sensor, such as an optically pumped magnetometer (OPM) as a measurement tool, which, in some embodiments, utilizes nonradioactive self-contained alkali metal cells coupled with a closed pumping laser and photodetector setup to measure minute magnetic fields. In some embodiments of the devices and systems described herein, the devices and systems utilize OPMs in an n×n array (or grid) or alternative geometric configuration to collect magnetic field data at n discrete locations over, for example, a portion of a body of an individual such as a chest area, which, in some embodiments, is digitized using pickup electronics.

OPMs are typically configured to utilize nonradioactive self-contained alkali metal cells coupled with a closed pumping laser and photodetector setup to measure minute magnetic fields. Compared to superconducting quantum interference devices (SQUIDs), which are typically also used to detect these biomagnetic fields, OPM sensors are significantly smaller and typically do not require the use of cryogenic cooling.

The Earth's magnetic field is naturally present everywhere on Earth, and the amplitude is about 50 microtesla. OPM performance is enhanced in at least two exemplary ways in the presence of the Earth's ambient magnetic field. In a first OPM enhancing technique, a reference value representing Earth's magnetic field is used as part of a vector subtraction to isolate a signal of interest in an OPM. Another technique involves the use of a gradiometer for active noise cancellation for the OPM.

A sensor array configuration, as utilized in some embodiments of the devices and systems described herein, comprises a custom array configuration. In some embodiments, a sensor array configuration is customized to an individual's anatomy. In some embodiments, a sensor array configuration is customized to a location on the individual which is measured, such as a chest location or a head location. In some embodiments, a sensor array configuration is customized to a measurement type that a device is programmed to acquire. In some embodiments, a sensor array configuration is customized to be operatively coupled with a shield and/or an arm. In some embodiments, a sensor array configuration is interchangeable with a different array configuration—a user may perform with interchange. An array configuration, in some embodiments, comprises an arc (such as a generally curved shape) having a depth and comprising a radius from about 20 cm to about 50 cm or from about 10 cm to about 60 cm. An array configuration, such as an arc configuration, in some embodiments, comprises one or more variable inter-magnetometer distances and variable sensor densities. An array configuration, in some embodiments, comprises a concave structure (such as a concave structure configured to wrap or form around a body region, such as a head or chest). One or more magnetometers is positioned on at least a portion of a surface of the concave structure. A concave array configuration, in some embodiments, comprises one or more variable inter-magnetometer distances and variable sensor density.

In some embodiments, a sensor array n×n sensors. In some embodiments, a sensor array is a 2D rectangular array, such as a 2×2 array or a 4×4 array. In some embodiments, a sensor array is a 2D non-rectangular array, such as a 2×1 array or a 4×1 array. In some embodiments, a sensor array is a circular array or a semicircular array, such as a 3D array of sensors positioned in an arc or concave structure. In some embodiments, a sensor array is a 2D array or a 3D array. In some embodiments, a sensor of a sensor array comprises x, y, and z coordinates. An array, in some embodiments, comprises a single sensor, such as n×n=1×1. An array, in some embodiments, comprises two sensors, such as n×n=2×1. An array, in some embodiments, comprises three sensors. An array, in some embodiments, comprises four sensors. An array, in some embodiments, comprises nine sensors. An array, in some embodiments, comprises sixteen sensors. An array, in some embodiments, comprises 25 sensors. An array, in some embodiments, comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 sensors or more. In some embodiments, a sensor array comprises 8 sensors. In some embodiments, a sensor array comprises 16 sensors. In some embodiments, a sensor array comprises a single sensor housed in a single housing. In some embodiments, a sensor array comprises a plurality of sensors housed in a single housing, such as a housing having multiple sensor configurations or changeable sensor configurations. In some embodiments, a sensor array comprises a plurality of sensors housed in a plurality of housings. In some embodiments, a sensor array comprises a plurality of sensors, each sensor housed in a separate housing. In some embodiments, a first sensor and second sensor of a sensor array is different. In some embodiments, a first sensor and a second sensor of a sensor array is the same. In some embodiments, each sensor of a sensor array is unique. In some embodiments, each sensor of a sensor array is identical. In some embodiments, a subset of sensors within a sensor array is unique. In some embodiments, a subset of sensors within a sensor array is identical. Spatial positioning of a sensor in a sensor array is adjustable, such as by a user or automated by a controller. In some embodiments, spatial positioning of a sensor in a sensor array is fixed. In some embodiments, a number of sensors in a sensor array is selected based on an application. In some embodiments, a number of sensors in a sensor array is selected based on a type of measurement or a location of a measurement. An array, in some embodiments, comprises a single channel array or a multi-channel array. In some embodiments, increasing a number of sensors of a sensor array increases a resolution of a measurement taken by the array. In some embodiments, a sensor array of sensors is densely packed, such as substantially adjacent or proximal one another. An array of sensors is sparsely spaced, such as having a spacing between one another. In some embodiments, a subset of sensors of a sensor array is densely packed. In some embodiments, a subset of sensors of a sensor array is sparsely spaced or densely spaced. In some embodiments, centerpoints of any two sensors of a densely packed subset of sensors is spaced less than about: 5, 4.5, 4, 3.5, 3, 2.5, 2, 1.5, 1, 0.5, 0.1 centimeters (cm) apart. In some embodiments, centerpoints of densely packed sensors is spaced centerpoint to centerpoint from about 0.1 cm to about 2.0 cm or from about 0.1 cm to about 1.5 cm or from about 1.0 cm to about 2.0 cm. In some embodiments, centerpoints of any two sensors of a sparsely packed subset of sensors is spaced more than about: 1.5, 2, 2.5, 3, 3.5, 4, 4.5, 5, 8, 10 cm apart. In some embodiments, centerpoints of sparsely packed sensors is spaced centerpoint to centerpoint from about 1.5 cm to about 3 cm or from about 2 cm to about 5 cm or from about 2.5 cm to about 8 cm. In some embodiments, a center point is a central location of a sensor, such as a central axis. In some embodiments, a centerpoint of a circular sensor is a central point at which all other edge points are of equal distance.

In some embodiments, a densely packed array indicates intermagnetometer placement of less than 1.5 cm, while magnetometer placement of greater than about 1.5 cm constitutes a sparsely packed array.

In some embodiments, a housing is configured to house a sensor or a sensor array of sensors. In some embodiments, the housing is configured to accommodate a single configuration of sensor spacing within the housing. In some embodiments, the housing is configured to accommodate multiple configurations of sensor spacing within the housing. In some embodiments, the housing accommodates (i) adjusting sensor spacing, such as a dense spacing or a sparse spacing, or (ii) varying a number of sensors within the array. In some embodiments, a housing is a universal housing for a plurality of arrays and array configurations.

In some embodiments, a sensor is configured to sense a presence of or measure a parameter of a magnetic field. A sensor, in some embodiments, comprises a sensitivity to a magnetic field of about 10 femtotesla per root Hertz (fT/√Hz). A sensor, in some embodiments, comprises a sensitivity of from about 1 fT/√Hz to about 20 fT/√Hz. A sensor, in some embodiments, comprises a sensitivity of from about 5 fT/√Hz to about 15 fT/√Hz. A sensor, in some embodiments, comprises a sensitivity of from about 0.1 fT/√Hz to about 30 fT/√Hz. A sensor, in some embodiments, comprises a sensitivity of from about 0.5 fT/√Hz to about 12 fT/√Hz. A sensor, in some embodiments, comprises a sensitivity of from about 1 fT/√Hz to about 15 fT/√Hz. A sensor, in some embodiments, comprises a sensitivity of about: 0.001, 0.005, 0.01, 0.05, 0.1, 0.5, 1, 2, 3, 4, 5, 6, 7, 8, 10, 11, 12, 13, 14, 15, 16, 17, 18, 19, 20 fT/√Hz.

In some embodiments, a sensor does not require a cooling element, such as cryogenic cooling, to collect a measurement. In some embodiments, a sensor collects a measurement over a temperature range of from about 30 degrees Fahrenheit (F) to about 110 degrees F. In some embodiments, a sensor collects a measurement over a temperature range of from about 50 degrees F. to about 110 degrees F. In some embodiments, a sensor collects a measurement over a time period of from about 1 second to about 5 hours without a need for a cooling element. In some embodiments, a sensor collects a measurement over a time period of from about 1 second to about 1 hour without a need for a cooling element. In some embodiments, a sensor collect a measurement over a time period of from about 1 second to about 30 minutes without a need for a cooling element.

A noise source, in some embodiments, comprises a magnetic field strength. In some embodiments, a strength of a magnetic field of a noise source is measured in units of Tesla (T). Noise, such as ambient noise, in some embodiments, comprises a magnetic field strength of less than about 100 nanotesla (nT). Noise, in some embodiments, comprises a magnetic field strength of less than about 1000 nT. Noise, in some embodiments, comprises a magnetic field strength of less than about 500 nT. Noise, in some embodiments, comprises a magnetic field strength of less that about 200 nT. Noise, in some embodiments, comprises a magnetic field strength of less than about 120 nT. Noise, in some embodiments, comprises a magnetic field strength of less than about 80 nT. A noise source, such as a magnetic field of the Earth, in some embodiments, comprises a magnetic field strength of about 50 microtesla (mT). Noise, in some embodiments, comprises a magnetic field strength of from about 40 mT to about 60 mT. Noise, in some embodiments, comprises a magnetic field strength of from about 10 mT to about 100 mT. Noise, in some embodiments, comprises an amplitude component, a frequency component, or a combination thereof, and, in some embodiments, comprises both sources that is direct current (DC), alternating current (AC), or a combination of the two.

Exemplary Applications

The systems, methods, devices, and software described herein are used in a number of different applications including in research and healthcare settings, wherein the systems, methods, devices, and software are used to evaluate a status of an individual and in some cases provide a diagnosis for a condition that the individual has. A condition may comprise both an abnormality (including a pre-disease condition) as well as a disease state. Exemplary types of disease evaluated by the systems, methods, devices, and software described herein include cardiac disease, neurologic disease, and gastrointestinal disease.

In some embodiments, devices, systems, software, and methods described herein provide a suggestion for a next diagnostic step to carry out with the individual following sensing and analyzing the EMF of the individual, such as, for example, an additional diagnostic test or modality that will assist in obtaining a diagnosis. Non-limiting examples of diagnostic modalities suggested include imaging, blood testing, and conduction monitoring (e.g. ECG and EEG).

In some embodiments, devices, systems, software, and methods described herein provide a suggestion for a treatment to be provided to an individual following sensing and analyzing the EMF of the individual.

(a) Cardiac Disease

In some embodiments, the systems, methods, devices, and software described herein are used to evaluate an individual for cardiac disease. Non-limiting examples of cardiac disease evaluated by the systems, methods, devices, and software described herein include CAD, arrhythmia, and congestive heart failure.

In some embodiments, the systems, methods, devices, and software described herein are used to evaluate an individual for CAD. In these embodiments, an EMF associated with a heart of an individual is sensed and based on the sensed EMF of the individual, a status of the individual is determined with respect to CAD. In some of these embodiments, a determination is made as to whether coronary disease is present in the individual. In some of these embodiments, a determination is made as to a degree of severity of a CAD that is present. A degree of severity determined, in some embodiments, comprises "severe," "moderate," or "mild," A degree of severity, in some embodiments, comprises a degree of a obstruction of one or more coronary vessels. For example, in some embodiments, an individual may be determined to have >90% obstruction of their Left Anterior Descending (LAD) artery, >80% obstruction of their LAD, >70% obstruction of their LAD, >60% obstruction of their LAD, or >50% obstruction of their LAD. In some embodiments, the systems, methods, devices, and software described herein determine a presence of a pre-CAD state or that a risk of developing coronary artery exists in the individual. For example, in some embodiments, it is determined that an individual has a >90% risk of developing moderate to severe CAD, a >80% risk of developing moderate to severe CAD, a >70% risk of developing moderate to severe CAD, or a >60% risk of developing moderate to severe CAD.

In some embodiments, the systems, methods, devices, and software described herein are used in an acute care setting to evaluate individuals with chest pain. For example, in some embodiments, individuals with left sided chest pain of unknown origin are ruled out of having CAD. For example, in some embodiments, individuals with left sided chest pain of unknown origin are ruled in for having CAD. In some embodiments, an individual with a normal ECG and/or at last one normal troponin level is assessed by the systems, devices, methods, and software described herein and determined to either have CAD, not have CAD, have a high likelihood of having CAD, or have a high likelihood of not having CAD.

More specifically, a system as described herein includes at least one EMF sensor (or a plurality of EMF sensors, or a plurality of EMF sensors arranged in an array) that are positioned in proximity to the heart of an individual. In some embodiments the system further comprises shielding to shield the at least one EMF sensor from ambient EMF readings. Once the at least one sensor senses an EMF, the sensed EMF is analyzed by the software described herein including a machine learning algorithm and a determination is made with respect to the status of the heart of the individual. In some embodiments, the analysis process comprises the generation, by the software described herein, of a visual representation of the EMF that is then analyzed. In some embodiments, a sensed EMF that shows a regular pattern without magnetic dipole dispersion, represents a normal finding, an absence of a presence of CAD in the individual, or a low likelihood of a presence of CAD in the individual. In some embodiments, a sensed EMF that shows an irregular pattern of magnetic pole dispersion represents an abnormal finding, a presence of CAD in the individual, or a high likelihood of a presence of CAD in the individual. In some embodiments, a shift in dipole angulation or significant disorganization in the magnetic field map (e.g. a triple pole) indicates a greater degree of vessel stenosis (i.e. greater degree of CAD).

In some embodiments, a suggestion for a treatment is provided. Non-limiting examples of treatments suggested for CAD include conservative treatment (e.g. improve diet and/or exercise), cholesterol lowering treatment, vasodilating medications, rhythm modulating medications, intravascular interventions including stenting, and bypass surgery.

(b) Neurological Disease

In alternative embodiments, the systems, methods, devices, and software described herein are used to evaluate an individual for neurological disease including abnormalities resulting from traumatic injury and stroke. Non-limiting examples of neurological disorders evaluated by the systems, methods, devices, and software described herein include epilepsy, stroke, traumatic brain injury, traumatic spine injury, encephalitis, meningitis, tumor, Alzheimer's disease, Parkinson's disease, ataxia, and psychiatric disorders including schizophrenia, depression, and bipolar disease.

(c) Gastrointestinal Disease

In alternative embodiments, the systems, methods, devices, and software described herein are used to evaluate an individual for gastrointestinal disease including any disease or disorder of any component of the gastrointestinal system including the gastrointestinal tract, the liver (including biliary system), and the pancreas. Non-limiting examples of gastrointestinal disorders evaluated by the systems, methods, devices, and software described herein include gastrointestinal cancers (including tumors of the gastrointestinal tract, liver, and pancreas), Crohn's disease, ulcerative colitis, irritable bowel disease, dismotility disorders, gall stones, colitis, cholangitis, liver failure, pancreatitis, and infections of the gastrointestinal system.

Methods

It should be understood, that any device, system, and/or software described herein is configured for use in or is captured by one or more steps of a method.

EXAMPLES

Cardiac Analysis

Figure 5A:
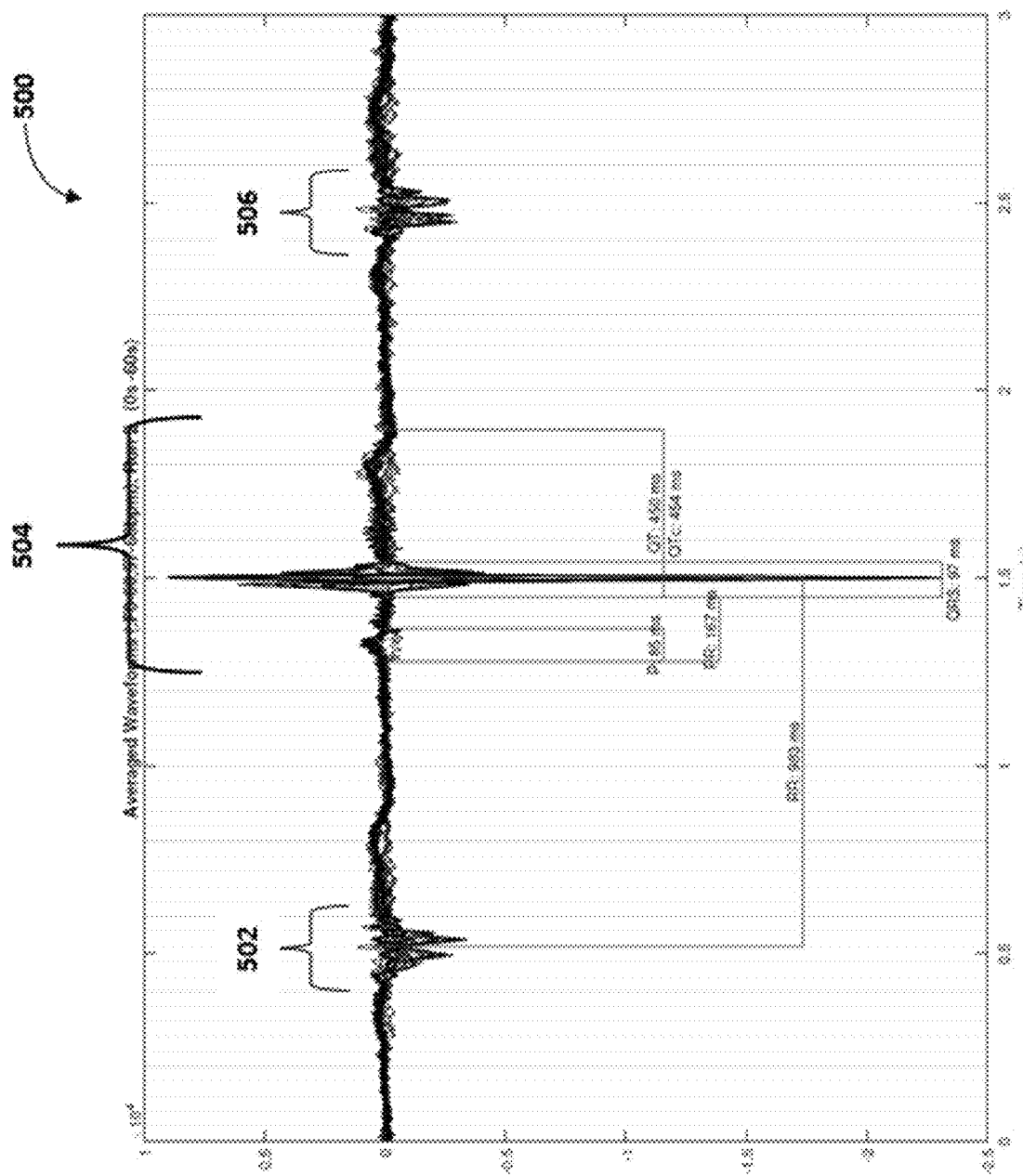
FIGS. 5A and 5B show examples of EMF data sensed from a plurality of OPM sensors positioned within proximity to a chest of an individual.

FIG. 5A shows an example of EMF data sensed from a plurality of OPM sensors positioned within proximity to a chest of an individual and, therefore, within proximity to a heart of the individual. The EMF sensed is associated with an electric current generated by cells of the heart of the individual. In this specific example, the EMF data that is sensed is from a 58 year old male using a plurality of OPM sensors positioned in proximity to the chest of the individual. The waveform 500 comprises EMF data in EM units (shown on the Y-axis), said data being sensed over time in seconds (shown on the X-axis).

More specifically, waveform 500 comprises a plurality of waveforms sensed from a plurality of OPM sensors positioned in proximity to the chest of the individual. In the example of FIG. 5A, the plurality of waveforms are positioned at different locations relative to the chest of the individual. In this example, the one or more OPM sensors are positioned in a sensor array where the array is itself positioned in proximity to the chest of the individual so that each of the plurality of OPM sensors is in a different position relative to the chest of the individual (although it should be understood that one or more OPM sensors may be arranged in other configurations in other embodiments of the systems, methods, devices, and software described herein and need not always be arranged in an array). In this example, waveform 500 comprises three separate individual waveforms 502, 504, and, 506. Waveforms 502, 504, and, 506 each correspond to a single PQRST complex as would be seen on a standard ECG. Therefore, each of the waveforms 502, 504, and, 506 correspond to an individual polarization and depolarization cardiac cycle or one heartbeat.

Figure 5B:
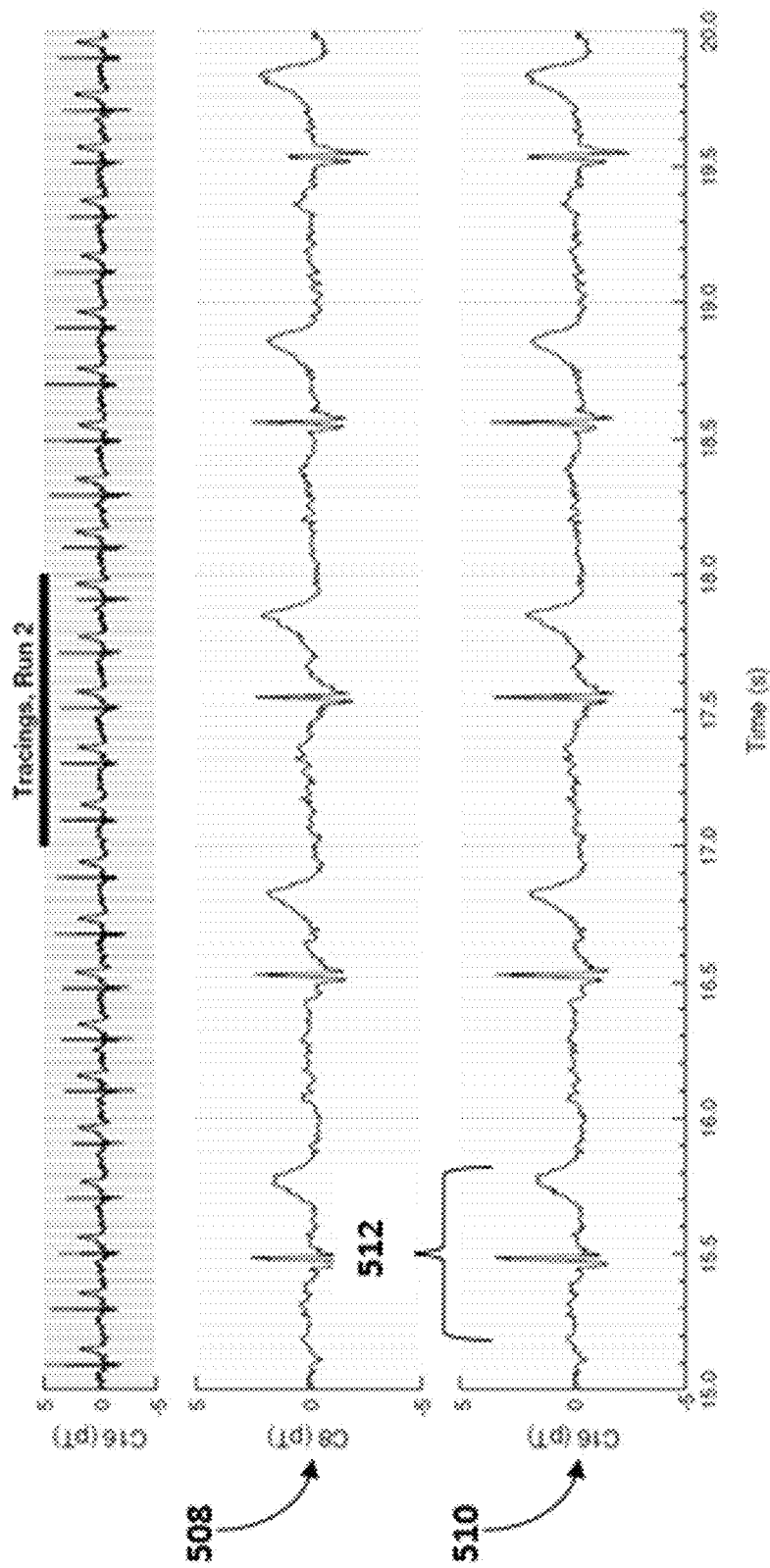

FIG. 5B shows examples of a plurality of single EMF waveforms (as compared to the single waveform of FIG. 5A which comprises a plurality of individual waveforms). In the examples of FIG. 5B, waveforms or tracings 508 and 510 each represent respective EMF signals sensed over the same period of time. In these examples, EMF data is sensed from the same 58 year old male using a plurality of OPM sensors as in the example of FIG. 5A. In the examples of FIG. 5B, tracings 508 and 510 are each a tracing representing a single waveform sensed over the same period of time and are different at least in part in that each of tracings 508 and 510 correspond to an EMF signal respectively sensed from a different OPM located at a different position relative to the chest (and therefore the heart) of the individual. That is, tracing 508 corresponds to a first EMF signal sensed from a first OPM sensor and tracing 510 corresponds to a second EMF signal sensed from a second OPM sensor where each of the first and second OPM sensors are located at different positions relative to the heart of the individual.

In a traditional ECG tracing, ten electrodes positioned at different locations on a body of an individual produce 12 ECG tracings, each corresponding to a different "view" of the heart. A particular ECG lead corresponds to a particular "view" of the heart in that each ECG tracing corresponds to a different spatial relationship between one or more ECG electrodes and the heart of the individual.

Similar to a traditional ECG tracing, each of tracings 508 and 510 represent a different "view" of the heart based on the position of the one or more EMF sensors relative to the chest of the individual. That is, current traveling through the heart of an individual generates a different EMF at different locations and as such is results in different appearing tracings based on the location of a sensor sensing that EMF. The tracings 508 and 510 each comprise a PQRST complex 512 (or, as shown, a plurality of PQRST complexes).

The exemplary data from FIGS. 5A and 5B are provided as input to a machine learning software module described herein. The machine learning software module receives the input and interrelates the data in numerous ways so that input data relating to the individual (including data related to the individual received concurrently to the input as well as data related to the individual received before and subsequent to receiving the input) is associated with the sensed EMF data shown in the examples of FIGS. 5A and 5B.

A machine learning software module as described herein correlates the age (58 years old in these examples) and gender (male in these examples) of the individual with one or more of the tracings 500, 508 and 510. Additional data relating to the individual may be provided that the machine learning software module may decide to correlate with the input as well. Non-limiting examples of the additional data comprises health records for the individual, including diagnoses, medications, lab results other EMF sensed data from the individual.

A machine learning software module as described herein further determines how to interrelate data from this individual and how to interrelate data of other individuals so as to generate a hypothesis function which is used to identify the presence of an abnormality in the individual and/or predict the occurrence of an abnormality in the individual.

Figure 6A:
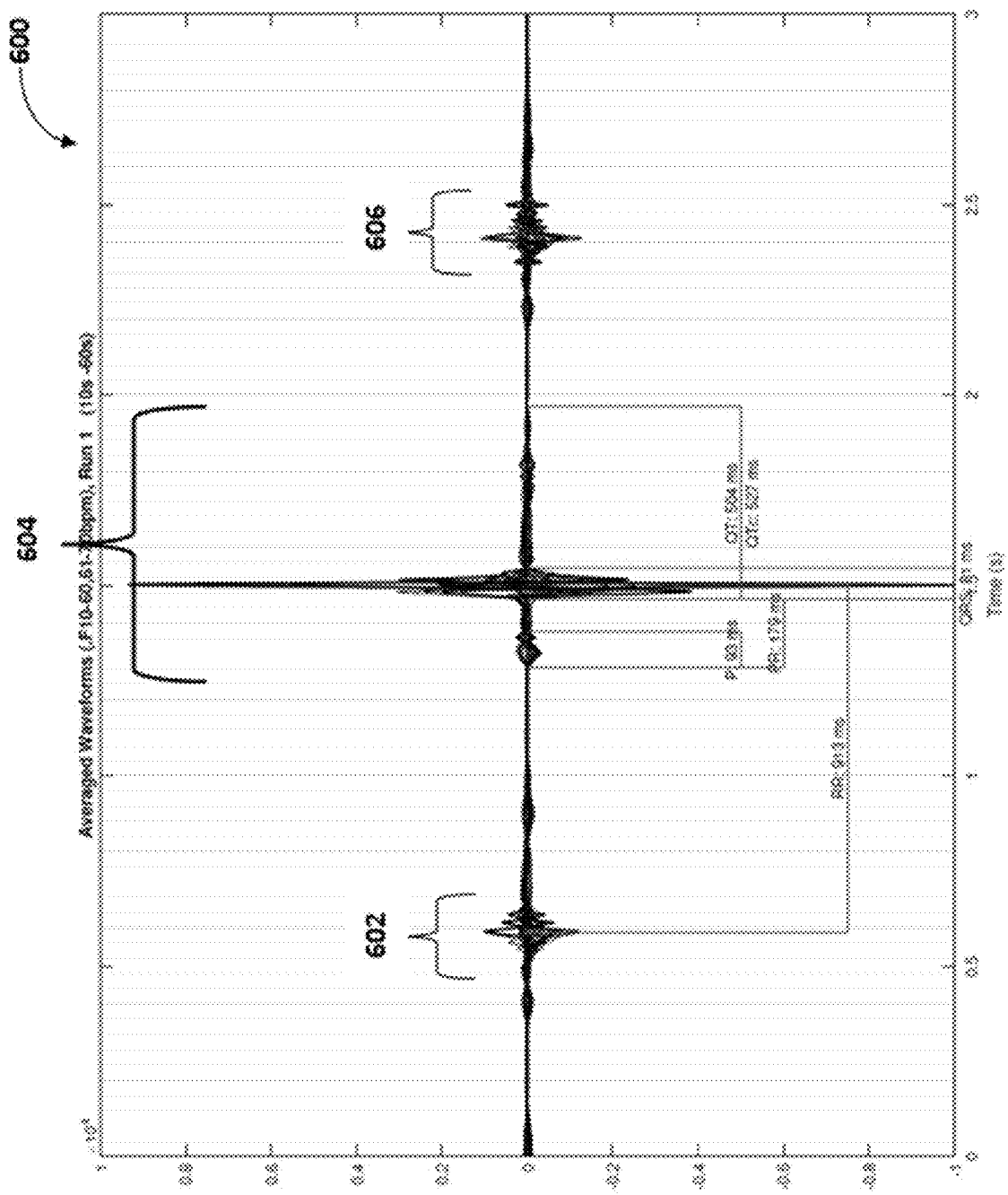
FIGS. 6A and 6B show examples of EMF data sensed from a plurality of SQUID sensors positioned within proximity to a chest of an individual.

FIG. 6A shows an example of EMF data sensed from a plurality of SQUID sensors positioned within proximity to a chest of an individual and, therefore, within proximity to a heart of the individual. The EMF sensed is associated with an electric current generated by cells of the heart of the individual. In this specific example, the EMF data that is sensed is from a 58 year old male using a plurality of SQUID sensors positioned in proximity to the chest of the individual. The waveform 600 comprises EMF data in EM units (shown on the Y-axis), said data being sensed over time in seconds (shown on the X-axis).

More specifically, waveform 600 comprises a plurality of waveforms sensed from a plurality of SQUID sensors positioned in proximity to the chest of the individual. In the example of FIG. 6A, the plurality of waveforms are positioned at different locations relative to the chest of the individual. In this example, the one or more SQUID sensors are positioned in a sensor array where the array is itself positioned in proximity to the chest of the individual so that each of the plurality of SQUID sensors is in a different position relative to the chest of the individual (although it should be understood that one or more SQUID sensors may be arranged in other configurations in other embodiments of the systems, methods, devices, and software described herein and need not always be arranged in an array). In this example, waveform 600 comprises three separate individual waveforms 602, 604, and, 606. Waveforms 602, 604, and, 606 each correspond to a single PQRST complex as would be seen on a standard ECG. Therefore, each of the waveforms 602, 604, and, 606 correspond to an individual polarization and depolarization cardiac cycle or one heartbeat.

Figure 6B:
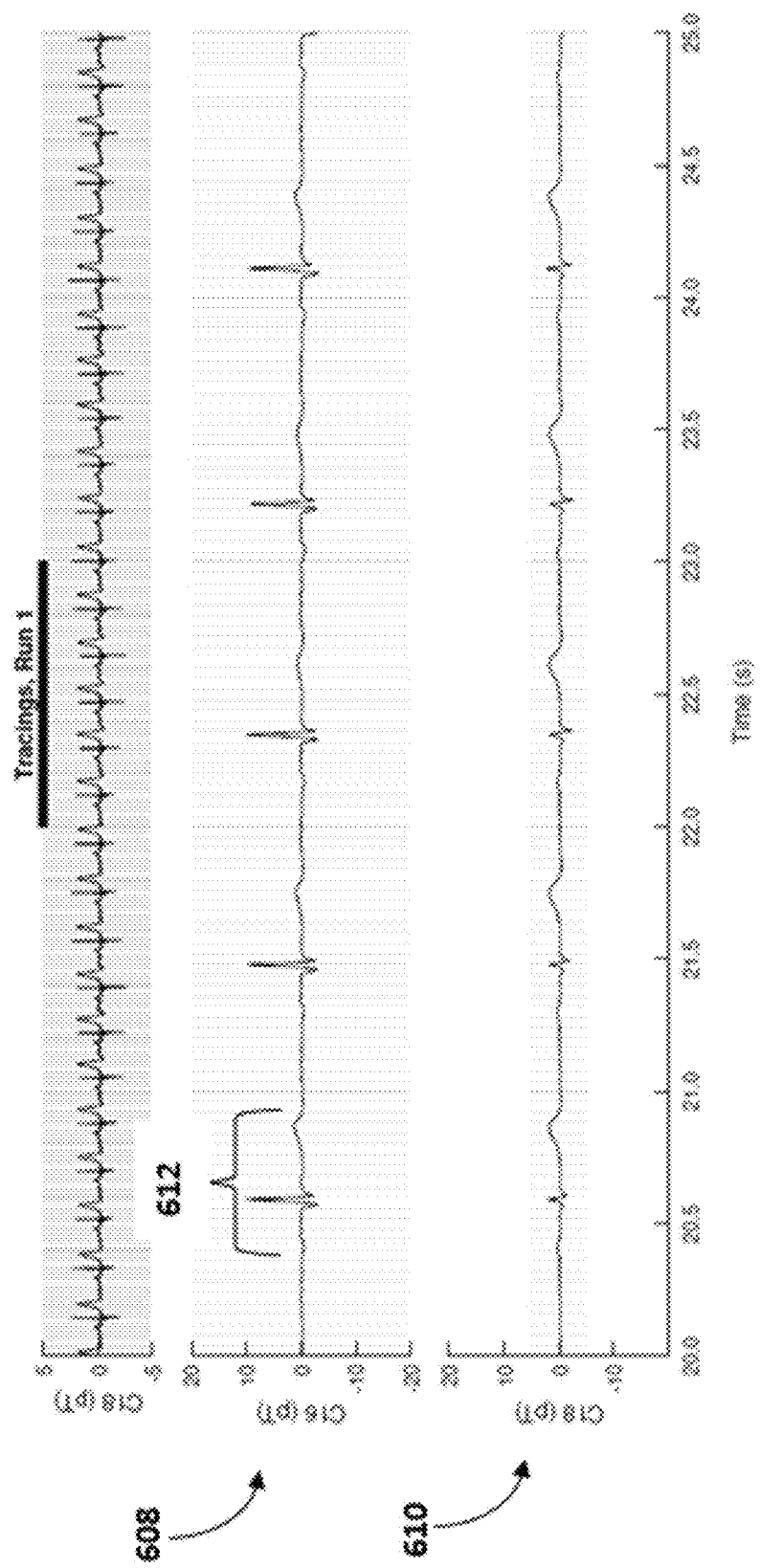

FIG. 6B shows examples of a plurality of single EMF waveforms (as compared to the single waveform of FIG. 6A which comprises a plurality of individual waveforms). In the examples of FIG. 6B, waveforms or tracings 608 and 610 each represent respective EMF signals sensed over the same period of time. In these examples, EMF data is sensed from the same 58 year old male using a plurality of SQUID sensors as in the example of FIG. 6A. In the examples of FIG. 6B, tracings 608 and 610 are each a tracing representing a single waveform sensed over the same period of time and are different at least in part in that each of tracings 608 and 610 correspond to an EMF signal respectively sensed from a different SQUID located at a different position relative to the chest (and therefore the heart) of the individual. That is, tracing 608 corresponds to a first EMF signal sensed from a first SQUID sensor and tracing 610 corresponds to a second EMF signal sensed from a second SQUID sensor where each of the first and second SQUID sensors are located at different positions relative to the heart of the individual.

In a traditional ECG tracing, ten electrodes positioned at different locations on a body of an individual produce 12 ECG tracings, each corresponding to a different "view" of the heart. A particular ECG lead corresponds to a particular "view" of the heart in that each ECG tracing corresponds to a different spatial relationship between one or more ECG electrodes and the heart of the individual.

Similar to a traditional ECG tracing, each of tracings 608 and 610 represent a different "view" of the heart based on the position of the one or more EMF sensors relative to the chest of the individual. That is, current traveling through the heart of an individual generates a different EMF at different locations and as such is results in different appearing tracings based on the location of a sensor sensing that EMF. The tracings 608 and 610 each comprise a PQRST complex 612 (or, as shown, a plurality of PQRST complexes).

The exemplary data from FIGS. 6A and 6B are provided as input to a machine learning software module described herein. The machine learning software module receives the input and interrelates the data in numerous ways so that input data relating to the individual (including data related to the individual received concurrently to the input as well as data related to the individual received before and subsequent to receiving the input) is associated with the sensed EMF data shown in the examples of FIGS. 6A and 6B.

A machine learning software module as described herein correlates the age (58 years old in these examples) and gender (male in these examples) of the individual with one or more of the tracings 600, 608 and 610. Additional data relating to the individual may be provided that the machine learning software module may decide to correlate with the input as well. Non-limiting examples of the additional data comprises health records for the individual, including diagnoses, medications, lab results other EMF sensed data from the individual.

A machine learning software module as described herein further determines how to interrelate data from this individual and how to interrelate data of other individuals so as to generate a hypothesis function which is used to identify the presence of an abnormality in the individual and/or predict the occurrence of an abnormality in the individual.

Figure 7A:
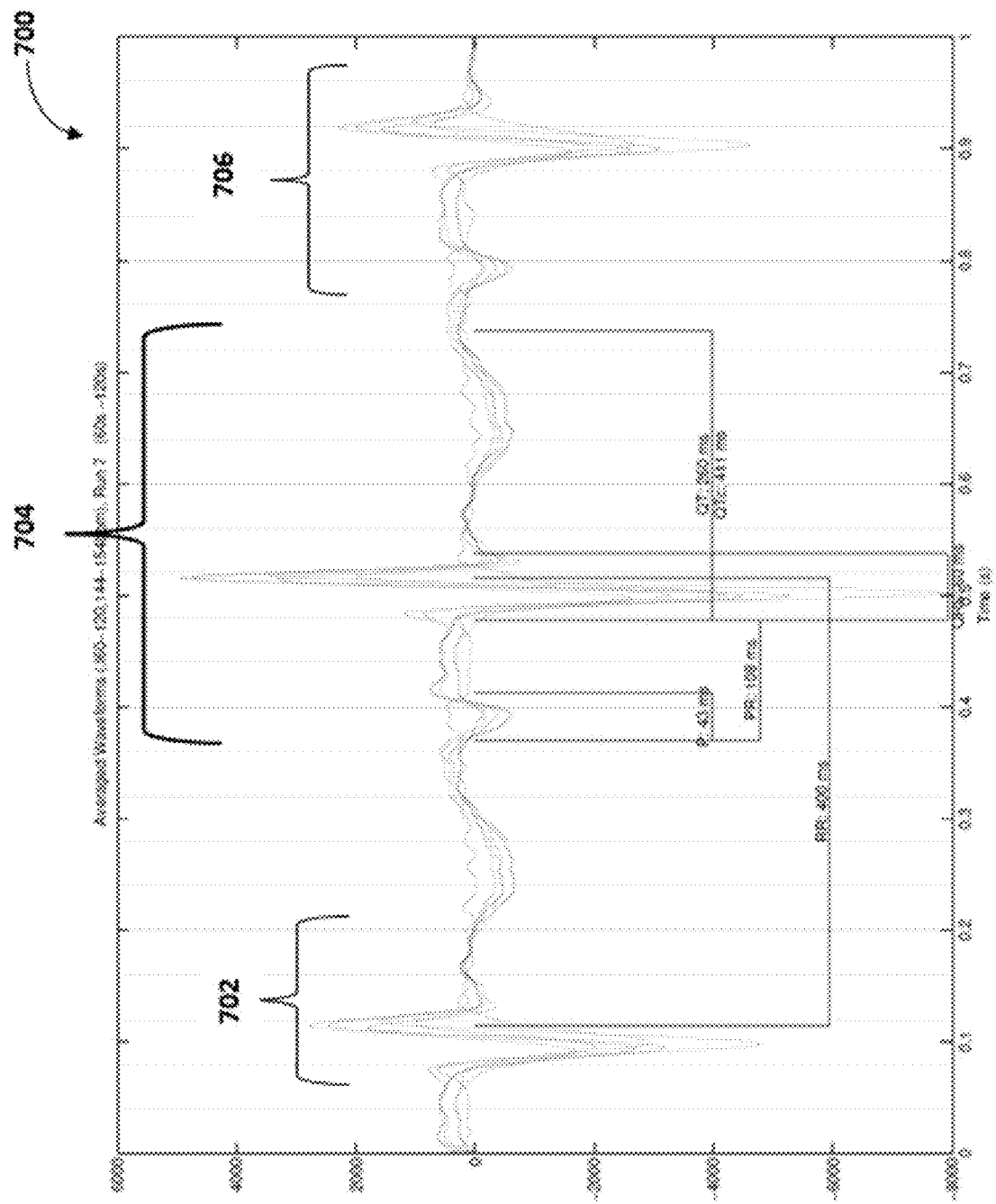
FIGS. 7A and 7B show examples of EMF data sensed from a plurality of OPM sensors positioned within proximity to a fetus.

FIG. 7A shows an example of EMF data sensed from a plurality of OPM sensors positioned within proximity to a heart of a fetus. In this specific example, the EMF data that is sensed is sensed from a 39 weeks and 6 days old fetus using a plurality of OPM sensors positioned in proximity to the fetus. The waveform 700 comprises EMF data in EM units (shown on the Y-axis), said data being sensed over time in seconds (shown on the X-axis).

More specifically, waveform 700 comprises a plurality of waveforms sensed from a plurality of OPM sensors positioned in proximity to the chest of the individual. In the example of FIG. 7A, the plurality of waveforms are positioned at different locations relative to the chest of the individual. In this example, the one or more OPM sensors are positioned in a sensor array where the array is itself positioned in proximity to the chest of the individual so that each of the plurality of OPM sensors is in a different position relative to the chest of the individual (although it should be understood that one or more OPM sensors may be arranged in other configurations in other embodiments of the systems, methods, devices, and software described herein and need not always be arranged in an array). In this example, waveform 700 comprises three separate individual waveforms 702, 704, and, 706. Waveforms 702, 704, and, 706 each correspond to a single PQRST complex as would be seen on a standard ECG. Therefore, each of the waveforms 702, 704, and, 706 correspond to an individual polarization and depolarization cardiac cycle or one heartbeat.

Figure 7B:
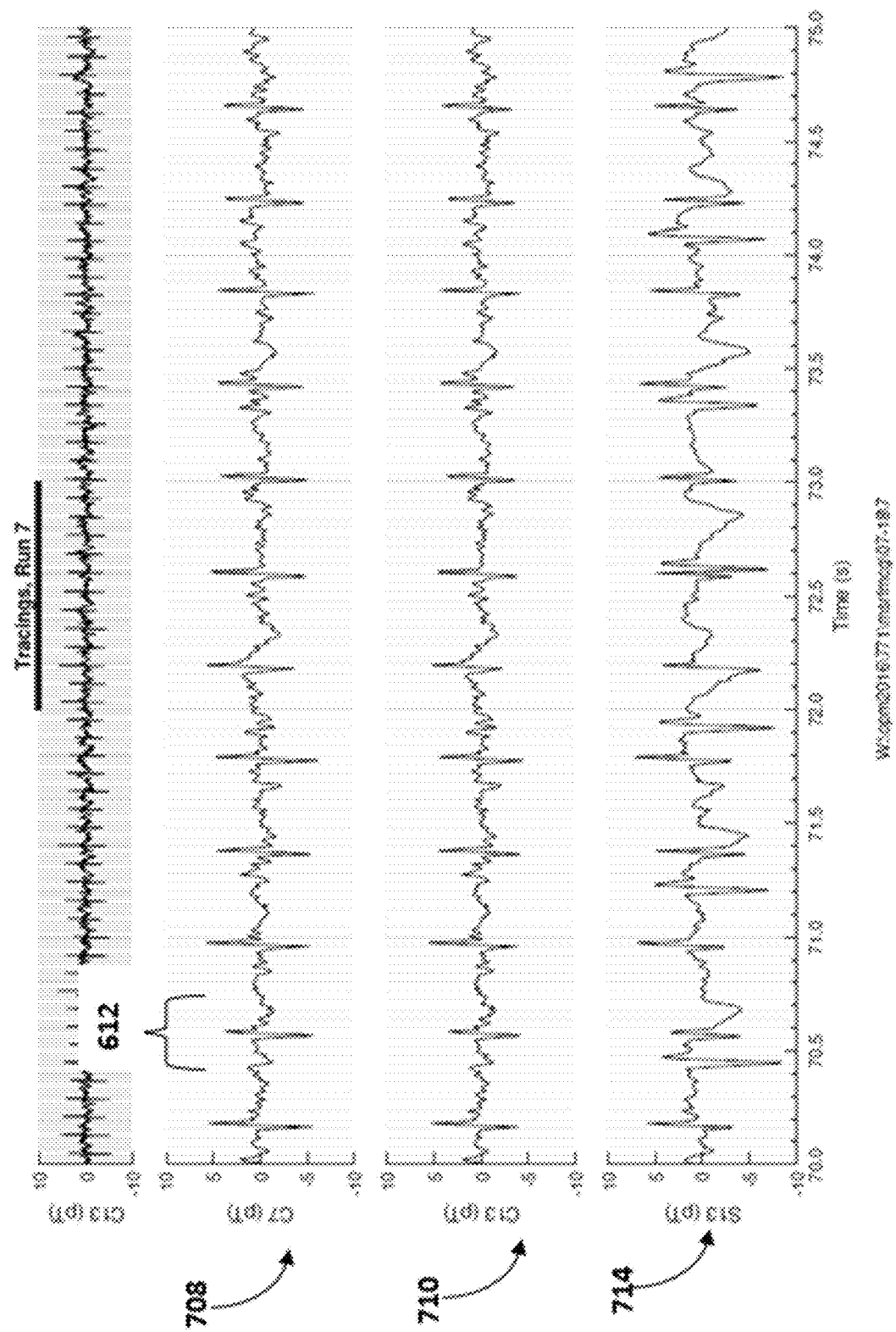

FIG. 7B shows examples of a plurality of single EMF waveforms (as compared to the single waveform of FIG. 7A which comprises a plurality of individual waveforms). In the examples of FIG. 7B, waveforms or tracings 708, 710, and 714 each represent respective EMF signals sensed over the same period of time. In these examples, EMF data is sensed from the same 39 weeks and 6 days old fetus using a plurality of OPM sensors as in the example of FIG. 7A. In the examples of FIG. 7B, tracings 708, 710, and 714 are each a tracing representing a single waveform sensed over the same period of time and are different at least in part in that each of tracings 708, 710, and 714 correspond to an EMF signal respectively sensed from a different OPM located at a different position relative to the chest (and therefore the heart) of the fetus. That is, tracing 708 corresponds to a first EMF signal sensed from a first OPM sensor and tracing 710 corresponds to a second EMF signal sensed from a second OPM sensor where each of the first and second OPM sensors are located at different positions relative to the heart of the fetus.

In a traditional ECG tracing, ten electrodes positioned at different locations on a body of an fetus produce 12 ECG tracings, each corresponding to a different "view" of the heart. A particular ECG lead corresponds to a particular "view" of the heart in that each ECG tracing corresponds to a different spatial relationship between one or more ECG electrodes and the heart of the fetus.

Similar to a traditional ECG tracing, each of tracings 708, 710, and 714 represent a different "view" of the heart based on the position of the one or more EMF sensors relative to the chest of the fetus. That is, current traveling through the heart of an fetus generates a different EMF at different locations and as such is results in different appearing tracings based on the location of a sensor sensing that EMF. The tracings 708, 710, and 714 each comprise a PQRST complex 712 (or, as shown, a plurality of PQRST complexes).

The exemplary data from FIGS. 7A and 7B are provided as input to a machine learning software module described herein. The machine learning software module receives the input and interrelates the data in numerous ways so that input data relating to the fetus (including data related to the fetus received concurrently to the input as well as data related to the fetus received before and subsequent to receiving the input) is associated with the sensed EMF data shown in the examples of FIGS. 7A and 7B.

A machine learning software module as described herein correlates the of the fetus with one or more of the tracings 700, 708, 710, and 714. Additional data relating to the fetus may be provided that the machine learning software module may decide to correlate with the input as well. Non-limiting examples of the additional data comprises health records for the fetus, including diagnoses, medications, lab results other EMF sensed data from the fetus.

A machine learning software module as described herein further determines how to interrelate data from this individual and how to interrelate data of other fetuses so as to generate a hypothesis function which is used to identify the presence of an abnormality in the individual and/or predict the occurrence of an abnormality in the fetus.

Figure 8A:
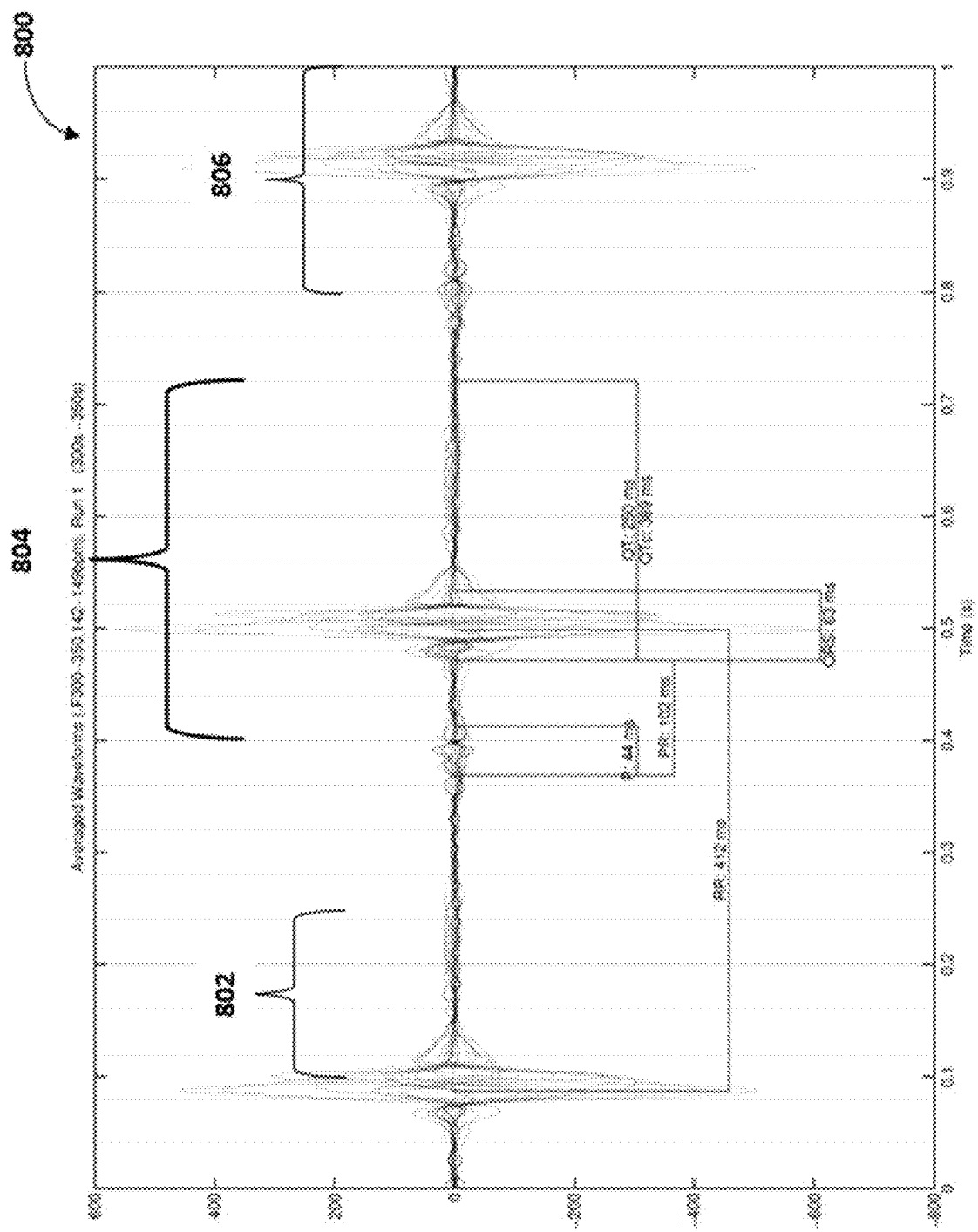
FIGS. 8A and 8B show examples of EMF data sensed from a plurality of SQUID sensors positioned within proximity to a fetus.

FIG. 8A shows an example of EMF data sensed from a plurality of SQUID sensors positioned within proximity to a heart of a fetus. In this specific example, the EMF that data is sensed is from a 39 weeks and 6 days old fetus using a plurality of SQUID sensors positioned in proximity to the fetus. The waveform 800 comprises EMF data in EM units (shown on the Y-axis), said data being sensed over time in seconds (shown on the X-axis).

More specifically, waveform 800 comprises a plurality of waveforms sensed from a plurality of SQUID sensors positioned in proximity to the chest of the individual. In the example of FIG. 8A, the plurality of waveforms are positioned at different locations relative to the chest of the individual. In this example, the one or more SQUID sensors are positioned in a sensor array where the array is itself positioned in proximity to the chest of the individual so that each of the plurality of SQUID sensors is in a different position relative to the chest of the individual (although it should be understood that one or more SQUID sensors may be arranged in other configurations in other embodiments of the systems, methods, devices, and software described herein and need not always be arranged in an array). In this example, waveform 800 comprises three separate individual waveforms 802, 804, and, 806. Waveforms 802, 804, and, 806 each correspond to a single PQRST complex as would be seen on a standard ECG. Therefore, each of the waveforms 802, 804, and, 806 correspond to an individual polarization and depolarization cardiac cycle or one heartbeat.

Figure 8B:
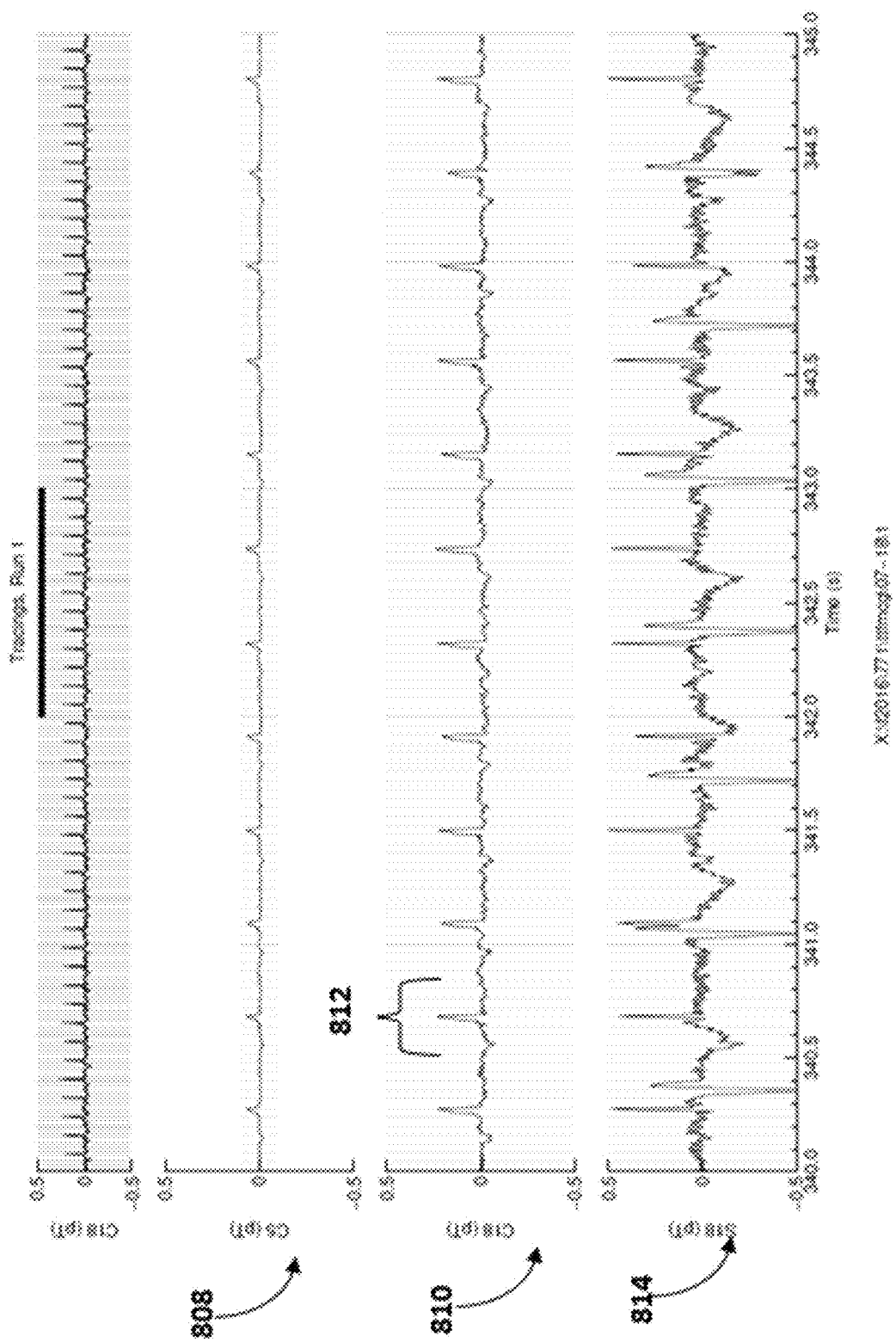

FIG. 8B shows examples of a plurality of single EMF waveforms (as compared to the single waveform of FIG. 8A which comprises a plurality of individual waveforms). In the examples of FIG. 8B, waveforms or tracings 808, 810, and 814 each represent respective EMF signals sensed over the same period of time. In these examples, EMF data is sensed from the same 39 weeks and 6 days old fetus using a plurality of SQUID sensors as in the example of FIG. 8A. In the examples of FIG. 8B, tracings 808, 810, and 814 are each a tracing representing a single waveform sensed over the same period of time and are different at least in part in that each of tracings 808, 810, and 814 correspond to an EMF signal respectively sensed from a different SQUID located at a different position relative to the chest (and therefore the heart) of the fetus. That is, tracing 808 corresponds to a first EMF signal sensed from a first SQUID sensor and tracing 810 corresponds to a second EMF signal sensed from a second SQUID sensor where each of the first and second SQUID sensors are located at different positions relative to the heart of the fetus.

In a traditional ECG tracing, ten electrodes positioned at different locations on a body of an fetus produce 12 ECG tracings, each corresponding to a different "view" of the heart. A particular ECG lead corresponds to a particular "view" of the heart in that each ECG tracing corresponds to a different spatial relationship between one or more ECG electrodes and the heart of the fetus.

Similar to a traditional ECG tracing, each of tracings 808, 810, and 814 represent a different "view" of the heart based on the position of the one or more EMF sensors relative to the chest of the fetus. That is, current traveling through the heart of an fetus generates a different EMF at different locations and as such is results in different appearing tracings based on the location of a sensor sensing that EMF. The tracings 808, 810, and 814 each comprise a PQRST complex 812 (or, as shown, a plurality of PQRST complexes).

The exemplary data from FIGS. 8A and 8B are provided as input to a machine learning software module described herein. The machine learning software module receives the input and interrelates the data in numerous ways so that input data relating to the fetus (including data related to the fetus received concurrently to the input as well as data related to the fetus received before and subsequent to receiving the input) is associated with the sensed EMF data shown in the examples of FIGS. 8A and 8B. A machine learning software module as described herein correlates, for example, the age the fetus with one or more of the tracings 800, 808, 810, and 814. Additional data relating to the fetus may be provided that the machine learning software module may decide to correlate with the input as well. Non-limiting examples of the additional data comprises health records for the fetus, including diagnoses, medications, lab results other EMF sensed data from the fetus.

A machine learning software module as described herein further determines how to interrelate data from this fetus and how to interrelate data of other fetuses so as to generate a hypothesis function which is used to identify the presence of an abnormality in the fetus and/or predict the occurrence of an abnormality in the fetus.

Figure 9:
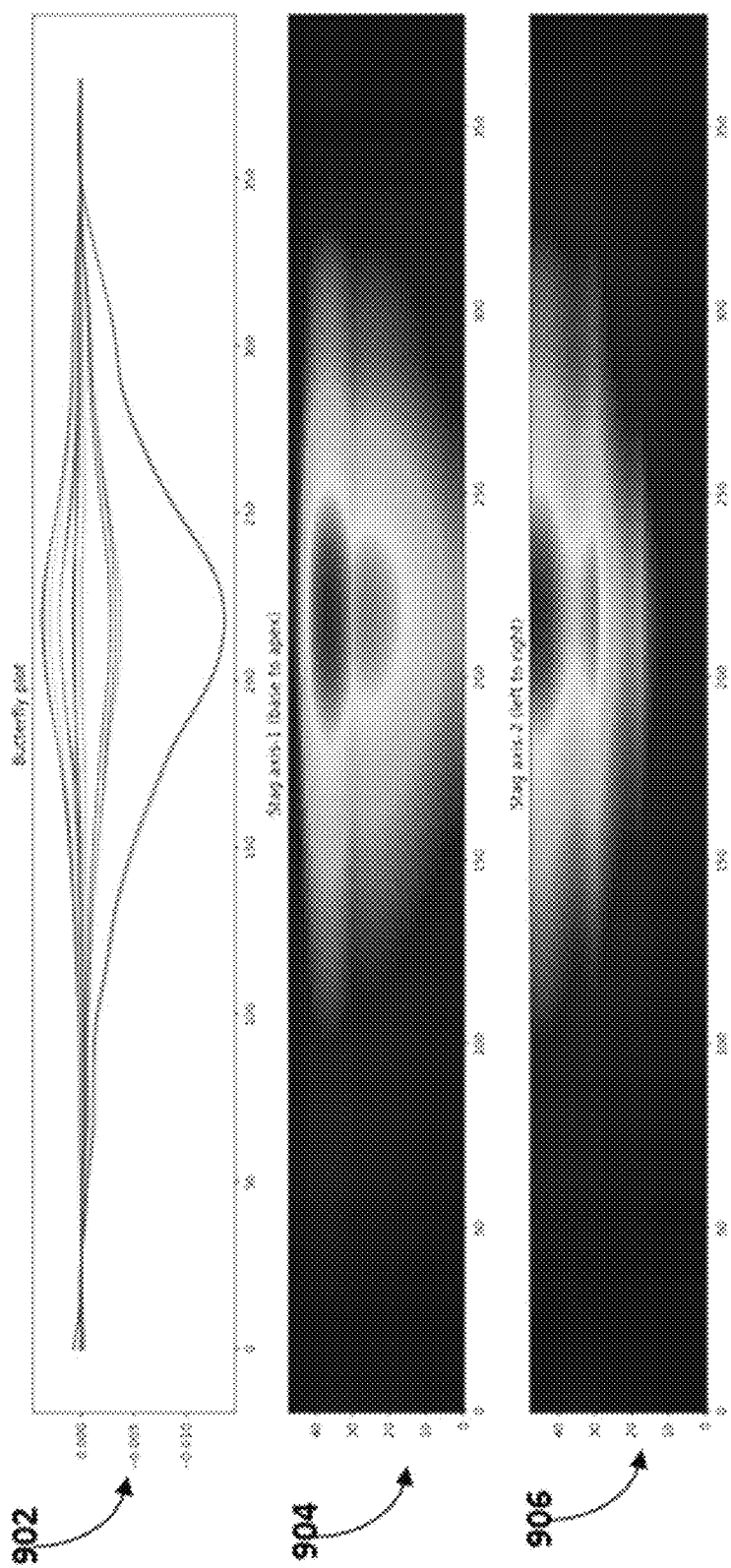
FIG. 9 shows three spatiotemporal activation representations of the magnetic activation of a healthy adult heart.

FIG. 9 shows three spatiotemporal activation representations of the magnetic activation of a healthy adult heart. The first spatiotemporal activation representation 902 comprises a butterfly plot. The second spatiotemporal activation representation 904 comprises a "view" of magnetic activation of a heart from base to apex. The third spatiotemporal activation representation 906 comprises a "view" of magnetic activation of a heart from left to right.

The exemplary data from FIG. 9 is provided as input to a machine learning software module described herein. The machine learning software module receives the input and interrelates the data in numerous ways so that input data relating to the individual from which the data was obtained (including data related to the individual received concurrently to the input as well as data related to the individual received before and subsequent to receiving the input) is associated with other sensed EMF data. A machine learning software module as described herein correlates, for example, the age the individual with other data relating to the individual. Additional data relating to the individual may be provided that the machine learning software module may decide to correlate with the input as well. Non-limiting examples of the additional data comprises health records for the individual, including diagnoses, medications, lab results other EMF sensed data from the individual.

A machine learning software module as described herein further determines how to interrelate data from this individual and how to interrelate data of other individuals so as to generate a hypothesis function which is used to identify the presence of an abnormality in the individual and/or predict the occurrence of an abnormality in the individual.

An Example Demonstrating Training and Prediction

Training Phase:

In an example of a neural network comprising a Deep Neural Network (DNN), the DNN is trained using 10,000 normal EMF data samples which are similar to the data sample of FIG. 9. These data samples are used by the neural network of this example to learn the probability distribution of normal EMF data. At the end of the training phase, the DNN determines or identifies or receives a hypothesis function which allows the DNN to generate high-quality reconstructions of normal repolarization (ST-T) segments from EMF data and minimize the reconstruction error between the original and the reconstructed input of normal EMF data.

Figure 10:
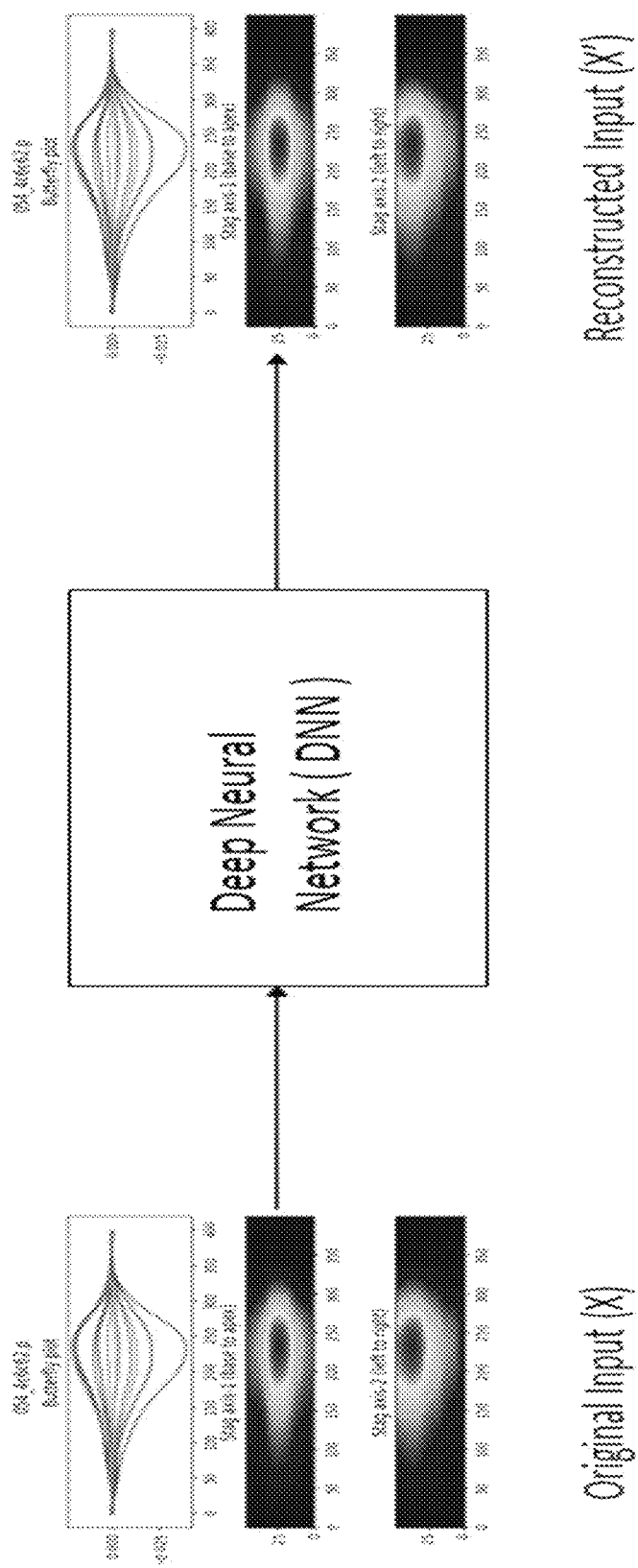
FIG. 10 shows a schematic representation of cardiac related EMF data received by a DNN which is configured to output a reconstruction of that EMF data X.

FIG. 10 shows a schematic representation of cardiac related EMF data received by a DNN which is configured to output a reconstruction of that EMF data X'. In this example, a hypothesis function used by the DNN to verify the accuracy of a reconstruction of EMF data compares the sensed input EMF data sample to the reconstruction generated by the DNN and determines a degree of error between the reconstruction and the input EMF data. The degree of error between the reconstruction generated by the DNN and the input EMF data is compared to a threshold value which is generated using the received 10,000 normal EMF data samples.

Prediction Phase:

A prediction phase uses the constructed and optimized hypothesis function from the training phase to predict the probability of an abnormality in an unknown patient's organ, tissue, body, or portion thereof by using the EMF data of the patient.

Based on the learned hypothesis function from the training phase, if the reconstruction error is greater than a particular threshold, the patient EMF data sample is abnormal.

Let T be the threshold, then hypothesis function H is defined as:

H=Reconstruction error (E) between the original input (X) and the reconstructed input (X')

$$H=E=X-X'$$

If E>=T→Abnormal, E<T→Normal

CAD Evaluation

As an example of how the systems, devices, methods, and software described herein are used to evaluate CAD, the following are the results of a clinical study in which individuals were evaluated for CAD as described herein:

Background and Importance

Cardiovascular disease remains the leading cause of death among men and women in the United States, representing over 25% all-cause mortality. (1) Approximately 8 million Americans present to the emergency department (ED) with chest pain making it the second most common chief complaint. (2) The majority of patients presenting to the ED are classified as low-to-intermediate cardiac risk and have non-diagnostic electrocardiograms and normal cardiac biomarkers. (2) These patients are frequently placed in an ED observation unit (EDOU) for further monitoring and diagnostic testing and utilize protocol-based management. (2) This can include stress testing and/or cardiology consultation. (3)

Genetesis, Inc. has developed a novel EMF analysis system that uses a series of diagnostic algorithms to convert EMF data into dynamic images that can indicate CAD or ischemia.

Goals of this Investigation

The aims of this pilot study were to (1) compare EMF sensing and analysis system with stress testing (ST) and/or coronary angiography (CA) to identify myocardial ischemia in EDOU chest pain patients, and (2) obtain information 30 days and 6 months post discharge of further diagnostic testing with ST or CA and major adverse cardiac events (MACE).

Study Design and Setting

This was a prospective observational pilot study of ED patients placed in an EDOU for evaluation of chest pain. The EDOU is a 30-bed unit located directly above the ED, staffed by emergency physicians. This study was approved by the hospital Institutional Review Board and registered in ClinicalTrials.gov.

Selection of Participants

ED chest pain patients with suspected acute coronary syndrome (ACS) placed in the EDOU for further evaluation were potentially eligible for the pilot study. Inclusion criteria included patients ≥18 years of age with low-intermediate risk chest pain defined as having no ACS diagnosis in the ED, a non-diagnostic ECG and two negative cardiac troponin T results at least 3 hours apart per ED protocol that consented to having an EMF sensing and analysis system scan. Exclusion criteria included patients with metallic items in the chest area, claustrophobia, non-ambulatory, in atrial fibrillation with rapid ventricular response, unable to fit into the EMF sensing and analysis system device or lie supine for 2 minutes, poor candidates for follow up (e.g. no access to a phone), prisoners, and repeat participants.

Data Collection and Processing

For eligible patients consents were obtained for study participation and 30-day and 6-month phone follow-up with release of medical information. Each patient was assigned a chronologic study number. Patients were scanned either prior to ST or CA, or immediately after ST. Patients traveled to the EMF sensing and analysis system comprised of a bed on rails and shielding chamber.

Figure 11:
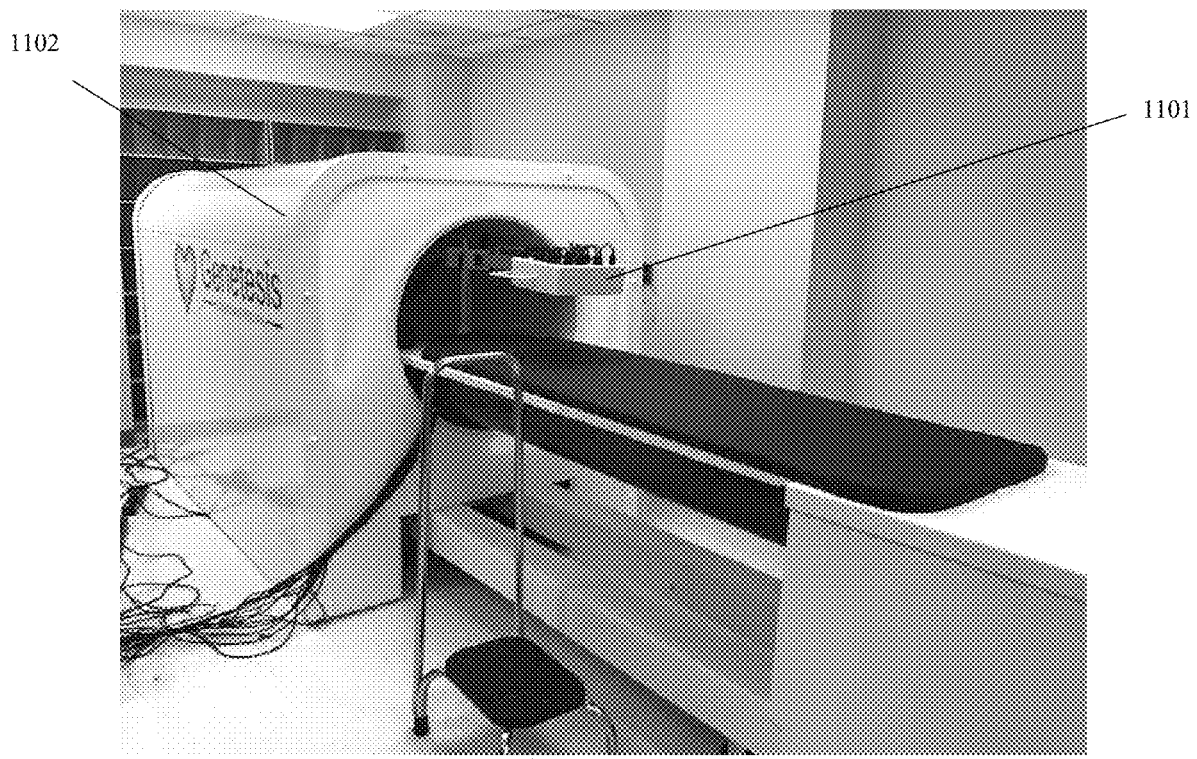
FIG. 11 shows an exemplary system as described herein which further configured to include one or more devices and software as described herein.

FIG. 11 shows an exemplary system as described herein which further configured to include one or more devices and software as described herein including an EMF sensor array (or sensor plate) 1101 and an ambient EMF shield 1102.

A sensor plate containing 14 sensors was positioned over the chest area and a 90 second-scan was obtained and stored in an encrypted database and sent to a HIPAA secure cloud. The EMF sensing and analysis system signal quality was evaluated by an automated function of the system software, and secondarily by Genetesis personnel. Sensed EMF data was aggregated and processed into 3 components: averaged EMF waveforms, Equivalent Current Dipole (ECD), and pseudocurrent density maps. ECD provides a mathematical model to measure and localize the movement of current wavefront within the myocardium at different points in the cardiac cycle. These components are analyzed by the system's software algorithms to look for significant deviations from a referenced database of normal images. The study team and Genetesis personnel were blinded to the results of EMF sensing and analysis system scans until after patient discharge from the index visit. A negative EMF sensing and analysis system scan was defined as current dipole deviation pattern findings correlating to <50% stenosis and a positive analysis result of the EMF sensing and analysis system as 50%-69% and ≥70% stenosis. CA was used as the gold standard if both ST and CA were performed.

Hospital data were collected using the hospital electronic medical record and included patient demographics, cardiac risk factors, cardiac co-morbidities, laboratory reports, consultant reports, diagnostic and operative reports, and discharge diagnosis.

Assessment of further diagnostic testing with ST or CA and MACE 30 days and 6 months post-discharge was performed via phone call to patients, primary physician and/or cardiologist as well as hospital electronic medical records.

Primary Data Analysis

Characteristics of the study group were described using the mean and standard deviation for continuous variables and frequency distributions for categorical variables. The sensitivity, specificity, positive and negative predictive value of the EMF sensing and analysis system scan results compared to the results from stress test and/or coronary catheterization were computed with associated confidence intervals. Data analysis were performed with SPSS v. 24.0.

Results

Of 125 consented patients, 101 underwent a scan using the EMF sensing and analysis system; 24 were excluded. Eleven patients were not scanned due to body habitus (5 patients), claustrophobia (3 patients), metal in thorax (1 patient), vasovagal episode (1 patient) or leaving the OU (1 patient) prior to scanning. Eleven inadequate scans occurred due to sensor railing; body habitus and patient movement contributed in 7 of these cases. Two patients were excluded as no ST or CA were performed to compare. For the 101 patients that underwent scan using the EMF sensing and analysis system, mean age was 56 years, 53.6% were male and 56.5% African American. A history of CAD was found in 9.9% (10/101) of patients, and 5.0% (5/101) had a history of heart failure or valvular heart disease. Mean number of cardiac risk factors was two and 28.7% (29/101) had 3 risk factors. ST were performed in 96% (97/101) of patients; 56% stress echocardiograms (SE), 17% dobutamine echocardiograms (DE), 27% persantine stress test (PST). Eighteen (17.8%) patients underwent CA. A normal EMF sensing and analysis system scan resulted in a regular pattern without magnetic dipole dispersion whereas an abnormal EMF sensing and analysis system scan demonstrated an irregular pattern of magnetic pole dispersion. It was theorized that an extreme shift in dipole angulation or significant disorganization in the magnetic field map (e.g. a triple pole) would indicate a greater degree of vessel stenosis.

Figure 12A:
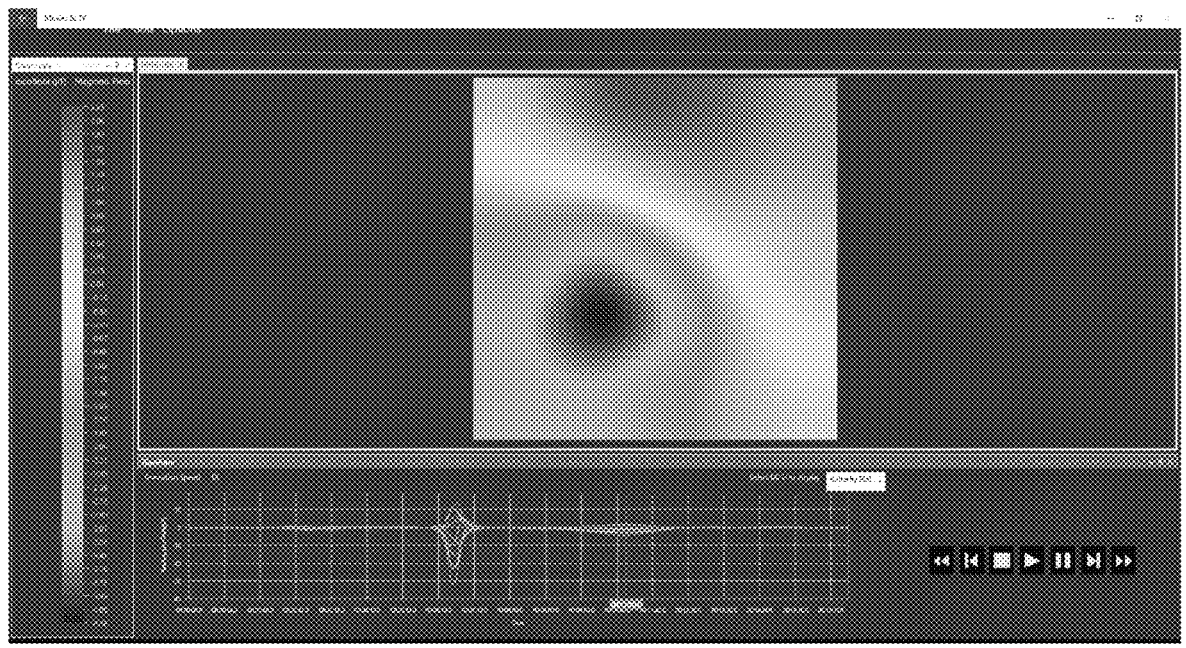
FIGS. 12A and 12B respectively show a negative result of a scan using an EMF sensing and analysis system as described herein, wherein FIG. 12A corresponds to a result of a first test subject and FIG. 12B corresponds to a test result of a second subject.
Figure 12B:
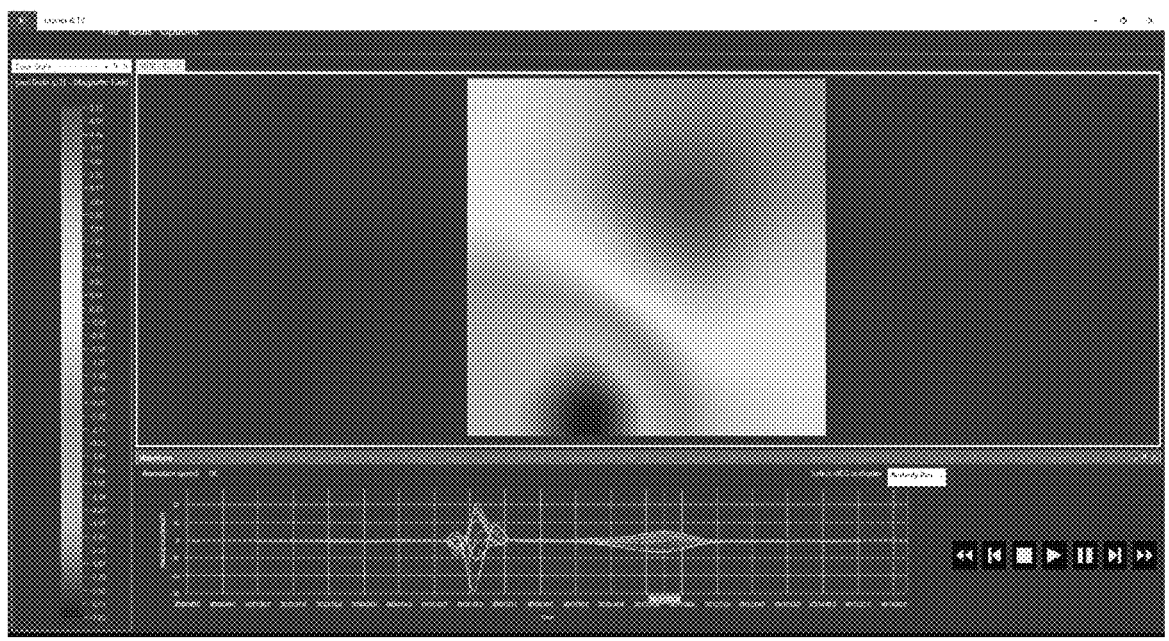

FIGS. 12A and 12B respectively show a negative result of a scan using an EMF sensing and analysis system as described herein, wherein FIG. 12A corresponds to a result of a first test subject and FIG. 12B corresponds to a test result of a second subject. More specifically, FIGS. 12A and 12B each show a regular pattern without magnetic dipole dispersion, which correspond to a negative result. The negative result in FIGS. 12A and 12B respectively indicate a negative result for the presence of CAD in the different test subjects.

Figure 13A:
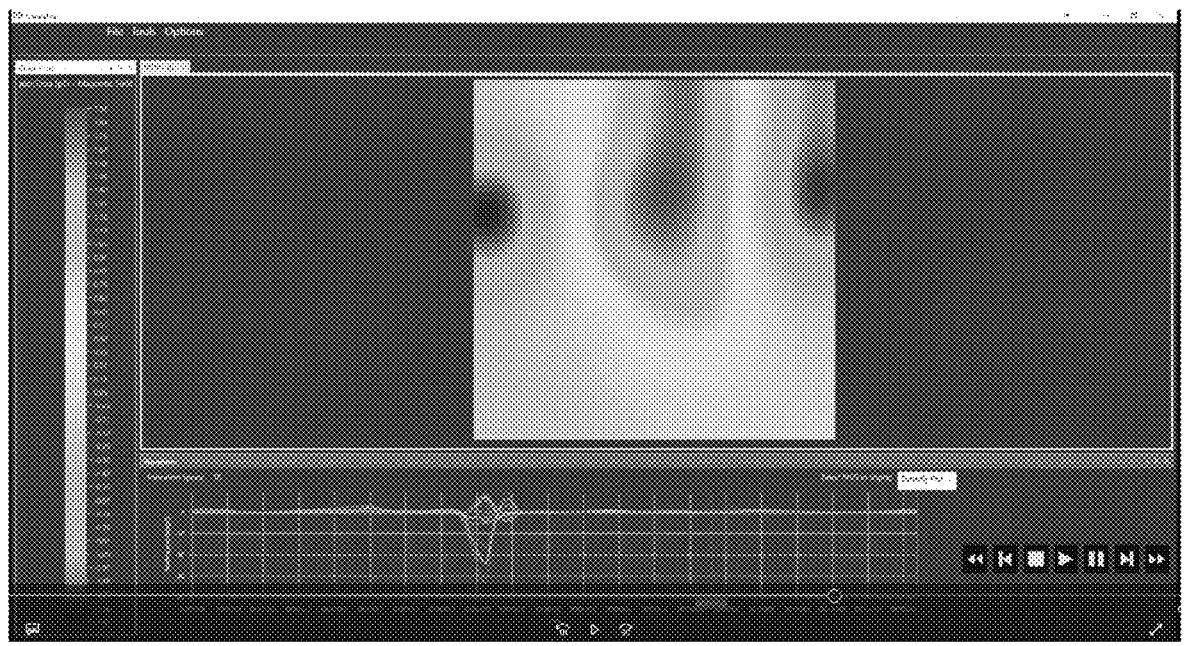
FIGS. 13A and 13B respectively show a positive result of a scan using an EMF sensing and analysis system as described herein, wherein FIG. 13A corresponds to a result of a first test subject and FIG. 13B corresponds to a test result of a second subject.
Figure 13B:
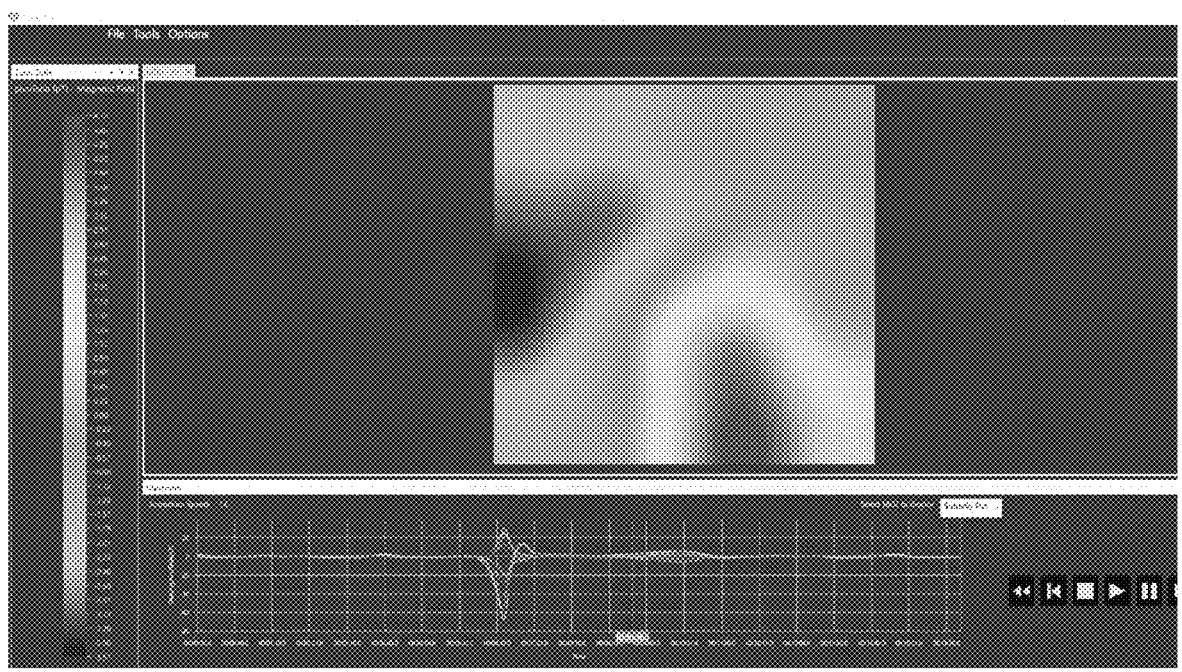

FIGS. 13A and 13B respectively show a positive result of a scan using an EMF sensing and analysis system as described herein, wherein FIG. 13A corresponds to a result of a first test subject and FIG. 13B corresponds to a test result of a second subject. More specifically, FIGS. 13A and 13B each show an irregular pattern of magnetic pole dispersion, which correspond to a positive result The positive result in FIGS. 13A and 13B respectively indicate a positive result for the presence of CAD in the different test subjects.

Of 78 patients with negative EMF sensing and analysis scans, 72 had corresponding negative ST (66) or CA (6), and 6 had positive ST (1) or CA (5).

Figure 14:
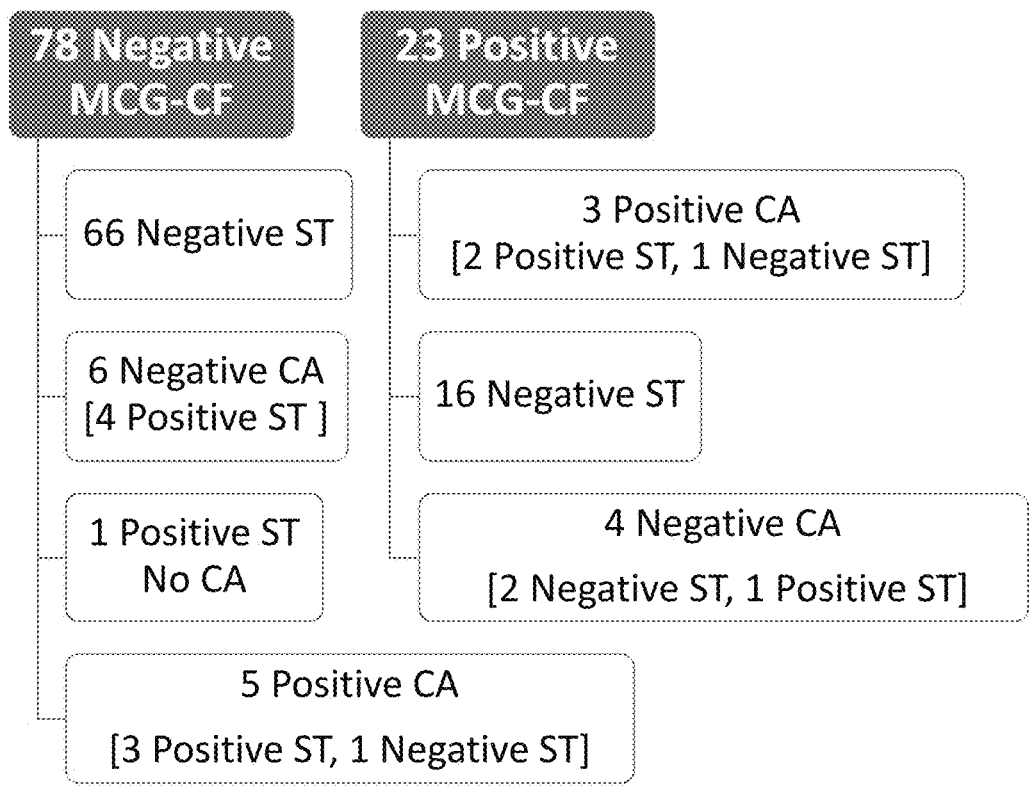
FIG. 14 shows a schematic representation of EMF sensing and analysis scan results as compared to CA and ST results.

FIG. 14 shows a schematic representation of EMF sensing and analysis scan results as compared to CA and ST results. Of 23 patients with a positive EMF sensing and analysis scan, 3 had a corresponding positive CA, and 20 had a negative ST (16) or CA (4). Only 9 patients in the entire cohort were positive for ischemia: ST (1), CA (8). All 3 patients with corresponding positive CA had ≥70% stenosis; EMF sensing and analysis scan interpreted as ≥70% in 2 of these patients (Stress Echocardiogram (SE) negative in one of these patients), and EMF sensing and analysis scan 50-69% (CA finding: 75% LAD) in the third. In 5 patients with non-corresponding positive CA (i.e. EMF sensing and analysis scan falsely negative), 4 patients had ≥70% stenosis on CA (one of these patients did not have a ST) and 1 had 60% stenosis also missed by SE. In 4 patients with non-corresponding negative CA (i.e. EMF sensing and analysis scan falsely positive), EMF sensing and analysis scan found 50-69% stenosis in 1 patient and ≥70% in 3 patients. Using ST or CA as the gold standard, the sensitivity with 95% CI for EMF sensing and analysis scan is 33.3% [7.5%, 70.7%], specificity 78.3% [68.4%, 86.2%], PPV 13% [5.2%, 29.0%] and NPV 92.3% [88.2%, 95.1%] for 50% stenosis and 28.6% [3.7%, 71.0%], 87.1% [78.6%, 93.2%], 14.3% [4.4%, 37.6%] and 94.2% [91.0%, 96.3%] respectively for 70% stenosis. Successful 30-day and 6-month phone follow-up was 25.7% and 18.8% respectively. Using both phone and electronic data, no patients underwent ST/CA or had MACE on 30-day follow-up. One patient underwent ST (negative) after an initial positive CA with stenting and two patients underwent CA (negative) on 6-month follow-up; both had corresponding negative EMF sensing and analysis scan and ST. There were no reported MACE 6-months post discharge.

Discussion

This is the first study to prospectively evaluate EMF sensing and analysis scan and examine the feasibility of using this novel technology in non-high risk EDOU chest pain patients. Results from this pilot study suggest that EMF sensing and analysis scan is a simple, rapid, non-invasive diagnostic modality that is feasible in an OU patient population and has excellent specificity and NPV for obstructive (50-69%) and especially critical (≥70%) stenosis. This compares favorably to reported pooled results of ST with imaging from multiple studies and metanalysis showing a specificity of 70-80% for identifying patients with 50% stenosis. (4)

Although only a quarter or less of patients could be contacted on phone follow-up, this in addition to review of hospital medical records found that no patients had a positive ST/CA or MACE up to 6 months post-discharge. Two patients with initial negative EMF sensing and analysis scans had a confirmed negative CA on 6-month follow-up.

As with new technologies involving computer algorithms, machine learning can improve accuracy. In this pilot study, EMF sensing and analysis scanning was compared to ST/CA using this novel technology initial computer algorithm. As this is new technology with the ability to learn and synthesize new information, an independent physician who was blinded to the study results performed an over-read of all scans. Results from this over-read varied for 17 of the scans. There were 14 EMF sensing and analysis scans initially false positive found to be negative on over-read; 11 with corresponding negative ST (5 SE, 3 DE, 3 PST) and 3 with negative CA. One EMF sensing and analysis scan initially false negative compared to CA (≥70%) was found to be positive on over-read. There were 2 EMF sensing and analysis scans that initially corresponded with ST or CA that on over-read was false positive (PST negative) or false negative (CA positive, SE negative). Using ST or CA as the gold standard, the sensitivity with 95% CI for physician EMF sensing and analysis scan over-reads is 33.3% [7.5%, 70.1%], specificity 94.4% [83.4%, 98.2%], PPV 37.5% [14.6%, 67.8%] and NPV 93.3% [89.8%, 95.7%] for 50% stenosis and 42.9% [9.9%, 81.6%], 94.4% [87.5%, 98.2%], 37.5% [15.2%, 66.7%] and 95.5% [91.8%, 97.6%] respectively for 70% stenosis.

For emergency physicians, ruling out cardiac ischemia in ED patients with undifferentiated chest pain is crucial. A non-invasive, 90-second diagnostic test requiring no radiation exposure or exercise that is comparable to ST for ruling out cardiac ischemia could be a game-changer in the evaluation of these patients. Instead of an extended length of stay in the ED or OU (5), testing could be completed in under 2 minutes. Incorporation into the ED workflow of chest pain evaluation at triage or further downstream in the ED workup of chest pain patients should be explored. The downstream cost benefits to patients and the hospital could be substantial.

Limitations of this study include the small number of patients, enrollment of patients from a single site and as a convenience sample, and low prevalence of significant disease in this study cohort. Additionally, several patients were either unable to be scanned or had inadequate scans due to body habitus, i.e. some part of the body (e.g. chest, abdomen) was touching the sensor plate and causing motion artifact or sensor railing.

Conclusion

Results of this pilot study of a novel diagnostic test show a resting 90-second EMF sensing and analysis scan has excellent specificity and NPV and is faster and comparable to ST in ruling out obstructive cardiac ischemia in an EDOU population of low-intermediate risk chest pain patients. Specificity and NPV improve further with physician over-read of EMF sensing and analysis scan. Due to low prevalence of disease in this study cohort, a larger study that also includes high-risk chest pain patients is needed to better assess the accuracy of EMF sensing and analysis scan in detecting cardiac ischemia.

REFERENCES (1) Heron M. Deaths: Leading Causes for 2014. Natl Vital Stat Rep. 2016; 65(5):1-96.
(2) Amsterdam E A, Kirk J D, Bluemke D A, Diercks D, Farkouh M E, Garvey J L, et al. Testing of low-risk patients presenting to the emergency department with chest pain: a scientific statement from the American Heart Association. Circulation. 2010; 122(17):1756-76.
(3) Moseley M G, Hawley M P, Caterino J M. Emergency department observation units and the older patient. Clin Geriatr Med. 2013; 29(1):71-89.
(4) Arbab-Zadeh A. Stress testing and non-invasive coronary angiography in patients with suspected CAD: time for a new paradigm. Heart Int. 2012; 7(1):e2.
(5) Reinhardt S W, Lin C J, Novak E, Brown D L. Noninvasive Cardiac Testing vs Clinical Evaluation Alone in Acute Chest Pain: A Secondary Analysis of the ROMI-CAT-II Randomized Clinical Trial. JAMA Intern Med. 2018; 178(2):212-9.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A diagnostic system configured to determine whether cardiac ischemia is present in an individual, the diagnostic system comprising:
   (1) an electromagnetic field sensor configured to be positioned outside of a body of the individual and not in contact with the body of the individual in order to non-invasively sense an electromagnetic field measurement generated by a heart of the individual;
   (2) a processor operably coupled to the electromagnetic field sensor; and
   (3) a non-transitory computer-readable storage medium encoded with software comprising a trained machine learning software module that is trained using training data comprising electromagnetic field data, wherein the software is executable by the processor and causes the processor to:
      (a) receive the electromagnetic field measurement from the electromagnetic field sensor; and
      (b) determine whether the cardiac ischemia is present in the heart of the individual based on the electromagnetic field measurement by analyzing the electromagnetic field measurement using the trained machine learning software module and without generating a map of the electromagnetic field measurement.

2. The system of claim 1, wherein the software is further configured to cause the processor to determine whether a coronary artery occlusion is present in the individual based on the electromagnetic field measurement.

3. The system of claim 2, wherein the coronary artery occlusion is determined to be present when the electromagnetic field measurement comprises an irregular pattern of magnetic pole dispersion.

4. The system of claim 2, wherein the coronary artery occlusion is determined to be present with a degree of occlusion of greater than 50%.

5. The system of claim 2, wherein the coronary artery occlusion is determined to be present with a degree of occlusion of greater than 70%.

6. The system of claim 2, wherein the coronary artery occlusion is determined to be present with a degree of occlusion of greater than 90%.

7. The system of claim 2, wherein the system is further configured to determine whether the cardiac ischemia is present in the heart of the individual, when the individual has at least one negative troponin value.

8. The system of claim 1, wherein system is further configured to determine whether the cardiac ischemia is present in the heart of the individual, when the individual has a normal electrocardiogram.

9. The system of claim 1, further comprising a sensor array, wherein the electromagnetic field sensor is positioned within the sensor array.

10. The system of claim 1, wherein the electromagnetic field sensor comprises an optically pumped magnetometer or a superconducting quantum interference device sensor.

11. The system of claim 1, wherein the training data used to train comprises heart-related data.

12. The system of claim 1, wherein the processor is further configured to generate a waveform from the electromagnetic field measurement.

13. The system of claim 1, wherein the software is further configured to cause the processor to determine a therapy for treating the individual based on whether the cardiac ischemia is determined to be present.

14. The system of claim 1, wherein the trained machine learning software module comprises a deep neural network.

15. The system of claim 14, wherein the deep neural network comprises a deep convolutional neural network (CNN), a deep dilated CNN, a deep recurrent neural network (RNN), a deep fully connected neural network, a deep generative model, a deep Boltzmann machine, a deep restricted Boltzmann machine, or a feed-forward neural network.

\* \* \* \* \*